(12) United States Patent
Meurer-Grimes et al.

(10) Patent No.: US 6,710,075 B2
(45) Date of Patent: Mar. 23, 2004

(54) THERAPEUTIC COMPOUNDS AND METHODS

(75) Inventors: Barbara Martha Meurer-Grimes, Gisborne (AU); Jin Yu, Balwyn (AU); Gino Luigi Vairo, Northcote (AU)

(73) Assignee: The Government of the State of Sarawak, Malaysia, Sarawak (MY)

( * ) Notice: Subject to any disclaimer, the term of this patent is extended or adjusted under 35 U.S.C. 154(b) by 0 days.

(21) Appl. No.: 10/291,863

(22) Filed: Nov. 8, 2002

(65) Prior Publication Data

US 2003/0181514 A1 Sep. 25, 2003

Related U.S. Application Data

(63) Continuation-in-part of application No. PCT/AU01/00810, filed on Jul. 5, 2001.

(30) Foreign Application Priority Data

Jul. 5, 2000 (AU) ................................................ PQ8665

(51) Int. Cl.[7] ..................... A61K 31/343; A61K 31/357; C07D 307/77; C07D 319/12
(52) U.S. Cl. ........................ 514/452; 514/468; 549/379; 549/458
(58) Field of Search ................................ 514/452, 468; 549/379, 458

(56) References Cited

U.S. PATENT DOCUMENTS

| | | | |
|---|---|---|---|
| 4,656,296 A | 4/1987 | Floyd | 549/379 |
| 6,420,393 B1 | 7/2002 | Guarnieri et al. | 514/337 |

FOREIGN PATENT DOCUMENTS

| | | |
|---|---|---|
| DE | 199 34 952 A1 | 2/2000 |
| JP | 9-67360 | 3/1997 |
| JP | 11-12279 | 1/1999 |
| WO | WO 96/04284 A1 | 2/1996 |
| WO | WO 97/08161 A1 | 3/1997 |
| WO | WO 00/7579 | 2/2000 |

OTHER PUBLICATIONS

Baumann, B. et al., "Rocaglamide Derivatives Are Potent Inhibitors of NF–κB Activation in T–Cells,"*Journal of Biological Chemistry*, 277(47):44791–44800, Nov. 22, 2002.

Bohnenstengel, F. et al., "1H–Cyclopental[b ]Benzofuran Lignans from Aglaia Species Inhibit Cell Proliferation and Alter Cell Cycle Distribution in Human Monocytic Leukemia Cell Lines," *Z. Naturforsch*, 54c, pp. 1075–1083, 1999.

Bohnenstengel, F. et al., "Structure Activity Relationships of Antiproliferative Rocaglamide Derivatives from Aglaia Species (Melicaceae)," *Z. Naturforsch*, 54c, pp. 55–60, 1999.

Brader, G. et al., "Bisamides, Lignans, Triterpenes, and Insecticidal Cyclopenta[b]Benzofurans from Aglaia Species,"*J. Nat. Prod.*, vol. 61, pp. 1482–1490, 1998.

Chaidir et al., "New Insecticidal Rocaglamide Derivatives from Flowers of Aglaia Duperreana (Meliaceae)," *Phytochemistry*, vol. 52, pp. 837–842, 1990.

Cui, B. et al., "Novel Cytotoxic 1H–Cyclopenta[b]Benzofuran Lignans from Aglaia Elliptica,"*Tetrahedron*, 53(52):17625–17632, 1997.

Davey, A. et al., "Synthesis of the Novel Anti–Leukaemic Tetrahydrocyclopenta[b]Benzofuran, Rocaglamide and Related Synthetic Studies," *J. Chem. Soc. Perkin Trans 1*, 1992.

Dreyer, M. et al., "New Insecticidal Rocaglamide Derivatives and Related Compounds from Aglaia Oligophylla, "*J. Nat. Prod.*, vol. 64, pp. 415–420, 2001.

Dr. Duke, "Phytochemical and Ethnobotanical Databases," *Agricultural Research Service; Ethnobotany Query*, pp. 1–2, Retrieved from <http://www.ars–grin.gov/cgi–bin/duke/ethnobot.p1> on Apr. 27, 2000.

Engelmeier, D. et al., "Cyclopenta[b]Benzofurans from Aglaia Species with Pronouned Antifungal Activity Against Rice Blast Fungus (Pyricularia Grisea)," *J. Agric. Food Chem.*, vol. 48, pp. 1400–1404, 2000.

Fuchs, B. et al., "Structure and Conformation of Heterocycles," *Tetrahedron*, 40(11):2011–2021, 1984.

Greger, H. et al., "Insecticidal Flavaglines and other Compounds from Fijan Aglaia Species," *Phytochemistry*, vol. 57, pp. 57–64, 2001.

Güssregen, B. et al., "New Insecticidal Rocaglamide Derivatives from Flowers of Aglaia Odorata," *Z. Naturforsch*, vol. 52c, pp. 339–344, 1997.

Hiort, J. et al., "New Insecticidal Rocaglamide Derivatives from the Roots of Aglaia Duperreana,"*J. Nat. Prod.*, vol. 62, pp. 1632–1635, 1999.

Ishibashi, F. et al., "Insecticidal 1H–Cyclopentatetrahydro [b]Benzofurans from Aglaia Odorata," *Phytochemistry*, 32(2):307–310, 1993.

Janprasert, J. et al., "Rocaglamide, A Natural Benzofuran Insecticide from Aglaia Odorata," *Phytochemistry*, 32(1):67–69, 1993.

King. M. et al., "X–Ray Crystal Structure of Rocaglamide, a Novel Antileukemic 1H–Cyclopenta[b]benzofuran from Aglaia Elliptifolia," *J. Chem. Soc., Chem. Commun.*, pp. 1150–1151, 1982.

Ko, F–N. et al., "PAF Antagonism in Vitro and in Vivo by Aglafoline from Aglaia Elliptifolia Merr," *European J. of Pharmacology*, vol. 218, pp. 129–135, 1992.

(List continued on next page.)

Primary Examiner—Taofiq Solola
(74) Attorney, Agent, or Firm—Seed IP Law Group PLLC

(57) ABSTRACT

The present invention provides compounds having a cyclopentabenzofuran core and the use of such compounds in therapy as well as compositions comprising said compounds.

34 Claims, 10 Drawing Sheets

OTHER PUBLICATIONS

Kraus, G. et al., "A Synthetic Approach to Rocaglamide via Reductive Cyclization of δ–Keto Nitriles," *J. Org. Chem.*, vol. 54, pp. 77–83, 1989.

Lee, S. et al., "Cytostatic Mechanism and Antitumor Potential of Novel 1h–Cyclopenta[b]benzofuran lignans isolated from Aglaia Elliptica," *Chemico–Biological Interactions*, vol. 115, pp. 215–228, 1998.

Mabberly, et al., *Flora Malesiana*, Series 1—Spermatophyta, vol. 12, part 1, pp. 261–265 amd 18–19, 1995.

Molleyres, L–P. et al., "Insecticidal Natural Products: New Rocaglamide Derivatives from Aglaia Roxburghiana," Extended Summaries: *IUPAC Congress*, pp. 494–497, 1999.

Nugroho, B. et al., "An Insecticidal Rocaglamide Derivatives and Related Compounds from Aglaia Odorata (Meliaceae)," *Phytochemistry*, vol. 51, pp. 367–376, 1999.

Nugroho, B. et al., "Insecticidal Rocaglamide Derivatives from Aglaia Duppereana," *Phytochemistry*, 44(8):1455–1461, 1997.

Nugroho, B. et al., "Insecticidal Rocaglamide Derivatives from Aglaia Elliptica and A. Harmsiana," *Phytochemistry*, 45(8):1579–1585, 1997.

Ohse, T., et al., "Chyclopentabenzofuran Lignan Protein Synthesis Inhibitors from Aglaia Odorata," *J. Nat. Prod.*, vol. 59, pp. 650–652, 1996.

Pannell, C., "A Taxonomic Monograph of the Genus Aglaia Lour. (Meliaceae)," *Key Bulletin Additional Series XVI*, pp. 201–206, 1992.

Pericàs, M. et al., "A Tool for Discriminating Between Steric and Electronic Effects in the Postion of the Conformational Equilibria of Substituted Dioxanes," *Tetrahedron*, 41(18):3785–3789, 1985.

Proksch, P. et al., "Chemistry and Biological Activity of Rocaglamide Derivatives and Related Compounds in Aglaia Species (Meliaceae), " *Current Organic Chemistry*, vol. 5, pp. 923–938, 2001.

Satasook, C. et al., "Activity of Rocaglamide, an Insecticidal Natural Product, Against the Variegated Cutworm, Peridroma Saucia (Lepidoptera : Noctuidae)," *Pestic. Sci.*, vol. 36, pp. 53–58, 1992.

Schneider, C. et al., "Insecticidal Rocaglamide Derivatives from Aglaia Spectabilis (Meliaceae)," *Phytochemistry*, vol. 54, pp. 731–736, 2000.

Trost, B. et al., "An Unusual Oxidative Cyclization. A Synthesis and Absolute Stereochemical Assignment of (–)—Rocaglamide," *J. Am. Chem. Soc.*, vol. 112, pp. 9022–9024, 1990.

Wang, S–W. et al., "Cytotoxic Cyclopenta[b]benzofuran Derivatives from the Stem Bark of Aglaia Formosana," *Plant Med*, vol. 67, pp. 555–557, 2001.

Wu, T–S. et al., "Cytotoxic and Antiplatelet Aggregation Principles from Aglaia Elliptifolia," *J. Nat. Prod.*, vol. 60, pp. 606–608, 1997.

Xu , X–J. et al., "Flavonol–Cinnamate Cycloadducts and Diamide Derivatives from Aglaia Laxiflora," *J. Nat. Prod.*, vol. 63, pp. 473–476, 2000.

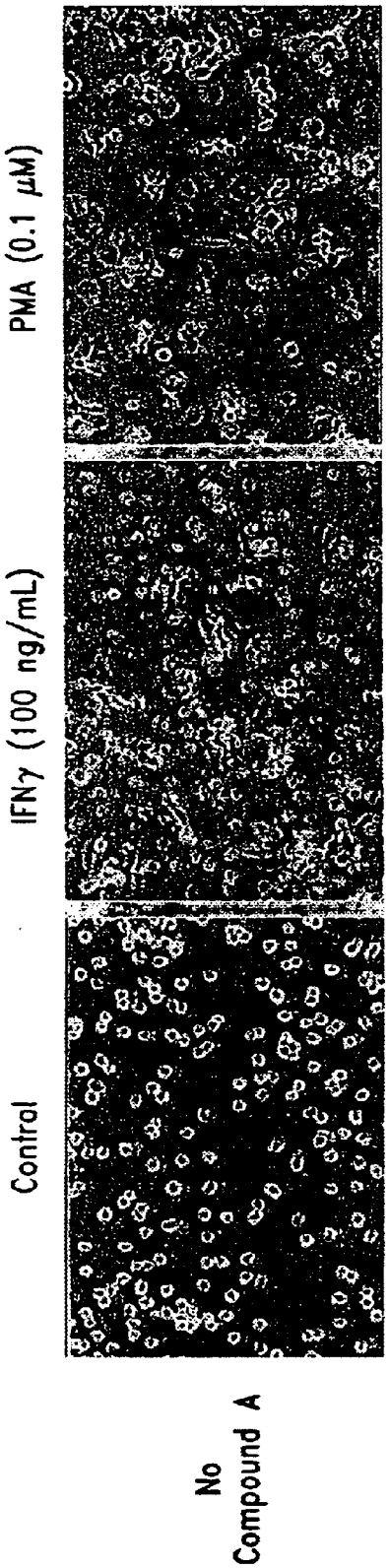

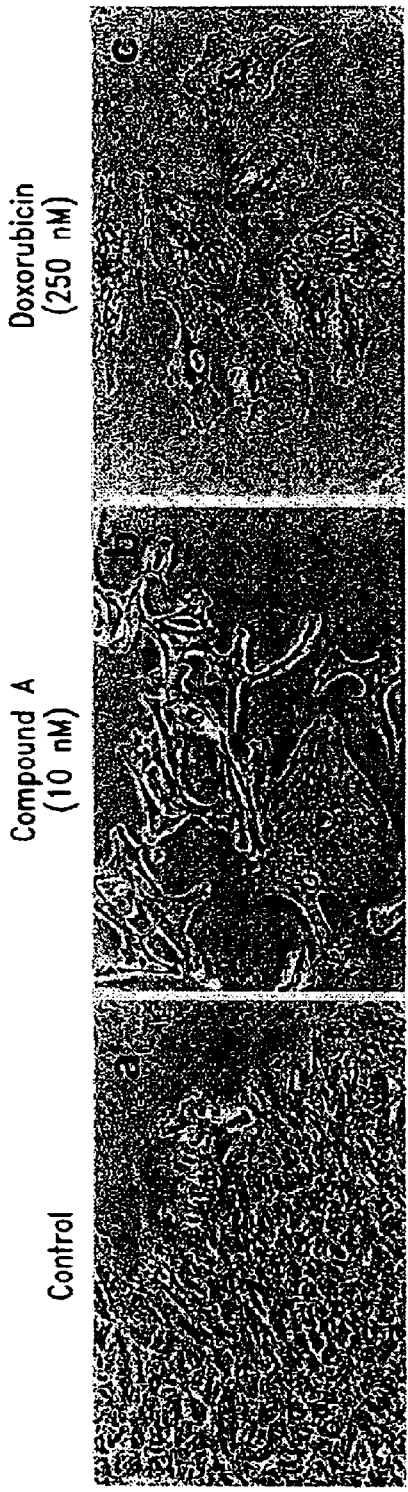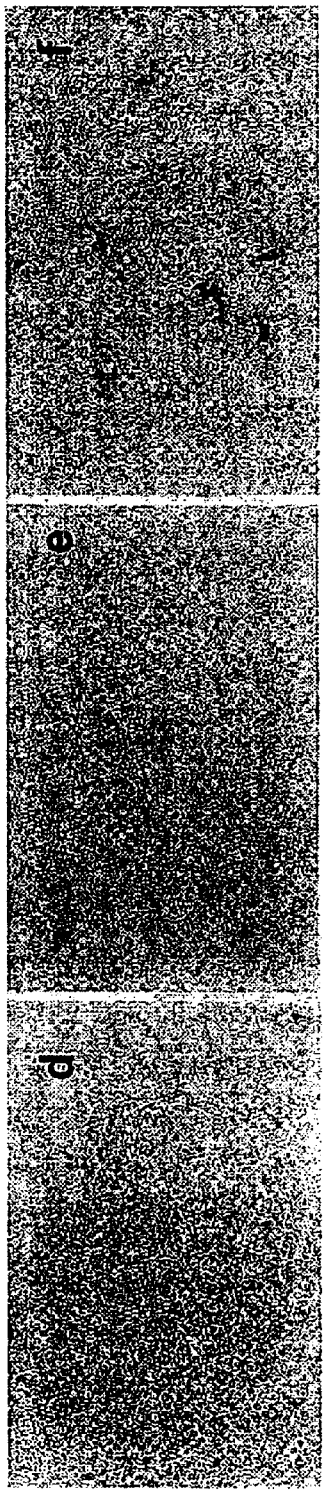
FIG. 9A  FIG. 9B  FIG. 9C
FIG. 9D  FIG. 9E  FIG. 9F

THERAPEUTIC COMPOUNDS AND METHODS

CROSS REFERENCE TO RELATED APPLICATIONS

The present application is a continuation-in-part of PCT/AU01/00810 filed Jul. 5, 2001.

FIELD OF THE INVENTION

The present invention relates generally to compounds having a cyclopentabenzofuran core. More particularly, the present invention relates to cyclopentabenzofuran compounds having a bulky substituent at the 6-oxy position, such as where the cyclopentabenzofuran core is substituted by a dioxanyloxy moiety. The invention also relates to the use of these compounds in therapy and compositions comprising said compounds.

BACKGROUND

Aglaia is a large genus of the family Meliaceac comprising over 100 (mostly woody) species in Indo-Malaysia and the Western Pacific region. Uses include treatment of fever, fractures, parturition and inflammation. Extracts are also used as bactericides, insecticides, in perfumery, as an astringent, tonic, a refrigerant (*Dr Duke's Phytochemical and Ethnobotanical Databases*) and for the treatment of abdominal tumours (Pannel, et al, 1992, Kew Bull., (16) 273–283).

More recently, a number of 1H-cyclopenta[b]benzofuran lignans have been isolated from Aglaia species (see for example, WO97/08161; JP 97171356; Ohse, et al, *J Nat Prod*, 1996, 59(7):650–52; Lee et al, Chem. Biol. Interact., 1998, 115(3):215–28; Wu et al, *J. Nat. Prod.*, 1997, 60(6):606–08; Bohnenstengel et al, *Z. Naturforsch*, 1999, 54c (12):55–60 and Bohnenstengel et al, *Z. Naturforsch*, 1999, 54c (12):1075–83, Xu, Y. J., et al, 2000, *J. Nat. Prod.*, 63, 4732–76, the entire contents of which are incorporated herein by reference). A number of these compounds have also been noted for their insecticidal activity (Janpraseri, et al, 1993, *Phytochemistry*, 32 (1): 67–69; Ishibashi et al, 1993, *Phytochemistry*, 32 (2): 307–310; Hiort, et al, 1999, *J. Nat. Prod.*, 62 (12): 1632–1635). Insecticidal compounds with a closely related core structure were isolated from Aglaia roxburghiana and are described in WO 9604284 for use as active ingredients in agrochemical formulations.

New compounds (Compounds A and B), as described herein) have now been isolated from Aglaia leptantha, Miq. (Meliaceae) which uniquely possess a dioxanyloxy group at the 6-position of the cyclopenta[b]benzofuran core. Compounds A and B have been shown to exhibit potent cytotoxic and cytostatic effects on cancer cell growth and viability and thus the compounds of the invention and derivatives thereof, may be useful as therapeutic agents in the treatment of cancer and cancerous conditions or other diseases associated with cellular hyperproliferation.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

In a first aspect, the invention relates to compounds of Formula (I) or a salt or prodrug thereof.

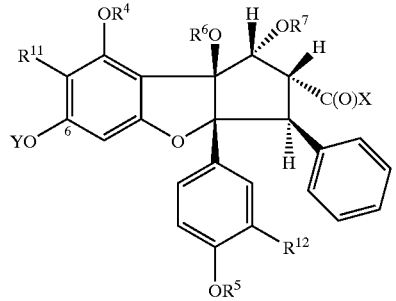

wherein
each $R^4$–$R^{10}$ is independently selected from the group consisting of hydrogen, optionally substituted alkyl, optionally substituted acyl, optionally substituted aryl, optionally substituted arylalkyl, optionally substituted cycloalkylalkyl, optionally substituted arylacyl, optionally substituted cycloalkylacyl and a C-1 linked saccharide;

X is $OR^8$ or $NR^9R^{10}$;

$R^{11}$ and $R^{12}$ are preferably each independently hydrogen or, alternatively, $OR^4$ and $R^{11}$, and/or $OR^5$ and $R^{12}$ together form a methylenedioxy group; and Y is selected from the group consisting of optionally substituted phenyl, optionally substituted benzyl, optionally substituted benzoyl, optionally substituted $C_3$–$C_8$ cycloalkyl, (preferably optionally substituted $C_5$–$C_6$ cycloalkyl) optionally substituted $CH_2$-($C_3$–$C_8$ cycloalkyl) (preferably optionally substituted $CH_2$-($C_5$–$C_6$ cycloalkyl), optionally substituted 5–6 membered heterocyclyl, and optionally substituted $CH_2$-(5–6 membered heterocyclyl).

In a preferred embodiment, the invention relates to compounds (including steroisomers within the dioxanyl group) of formula (i) or a salt or prodrug thereof.

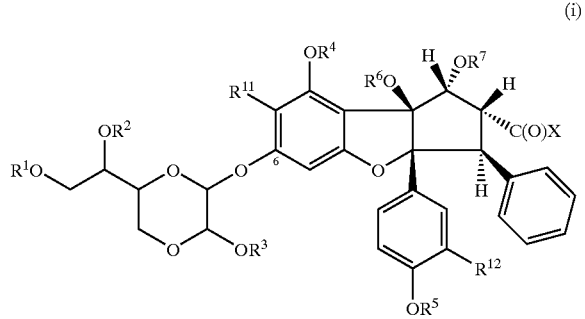

wherein
and each $R^1$–$R^{10}$ is independently selected from the group consisting of hydrogen, optionally substituted alkyl, optionally substituted acyl, optionally substituted aryl, optionally substituted arylalkyl, optionally substituted cycloalkylalkyl, optionally substituted arylacyl, optionally substituted cycloalkylacyl and a C-1 linked saccharide; and X is $OR^8$ or $NR^9R^{10}$);

$R^{11}$ and $R^{12}$ are each independently hydrogen or, $OR^4$ and $R^{11}$, and/or $OR^5$ and $R^{12}$ together form a methylenedioxy group. In one preferred embodiment, $R^{11}$ and $R^{12}$ are both hydrogen.

In one preferred embodiment, compounds of the present invention have the Formula (ii):

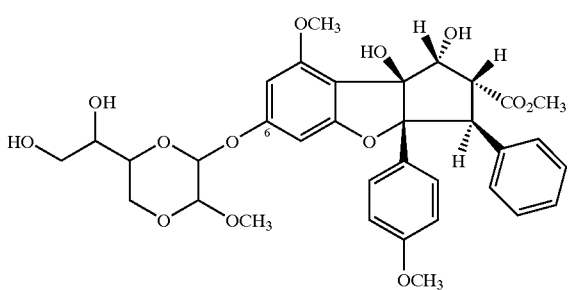

(ii)

or a salt or prodrug thereof.

Formula (ii) has 4 chiral centres in the dioxanyl moiety. Two isomers (isomeric in the dioxanyl group) of Formula (ii) have now been isolated—Compounds A and B as described in Example 1.

In another aspect, the invention provides a composition comprising a compound of Formula (I), such as Formula (i), or a salt or prodrug thereof, together with a pharmaceutically acceptable carrier, excipient or diluent.

In still a further aspect, the present invention provides a method for the treatment of cancer or a cancerous condition or a disease state or condition associated with cellular hyperproliferation comprising the administration of a treatment effective amount of a compound of Formula (I), such as Formula (i), or a salt, derivative or prodrug thereof, to a subject in need thereof. Some particular cancerous conditions which may be treated by the compounds of the invention may include lung, prostate, colon, brain, melanoma, ovarian, renal and breast tumours and leukemia. Disease states or conditions associated with cellular hyperproliferation which may be treated by compounds of the invention may include atherosclerosis, restinosis, rheumatoid arthritis, osteoarthritis, inflammatory arthritis, psoriasis, peridontal disease or virally induced cellular hyperproliferation.

BRIEF DESCRIPTION OF THE DRAWINGS

FIG. 1: Compound A Promotes Differentiation of THP-1 leukemic cells.

THP-1 cells were cultured for 4 days in the presence or absence of 10 nM Compound A as indicated. Where shown cells were also treated with IFNγ (100 ng/ml) (3 days) or with PMA (0.1 μM) (4 days) in the presence or absence of Compound A. Images are of cells visualised by phase contrast microscopy (magnification×200).

Figure 2:
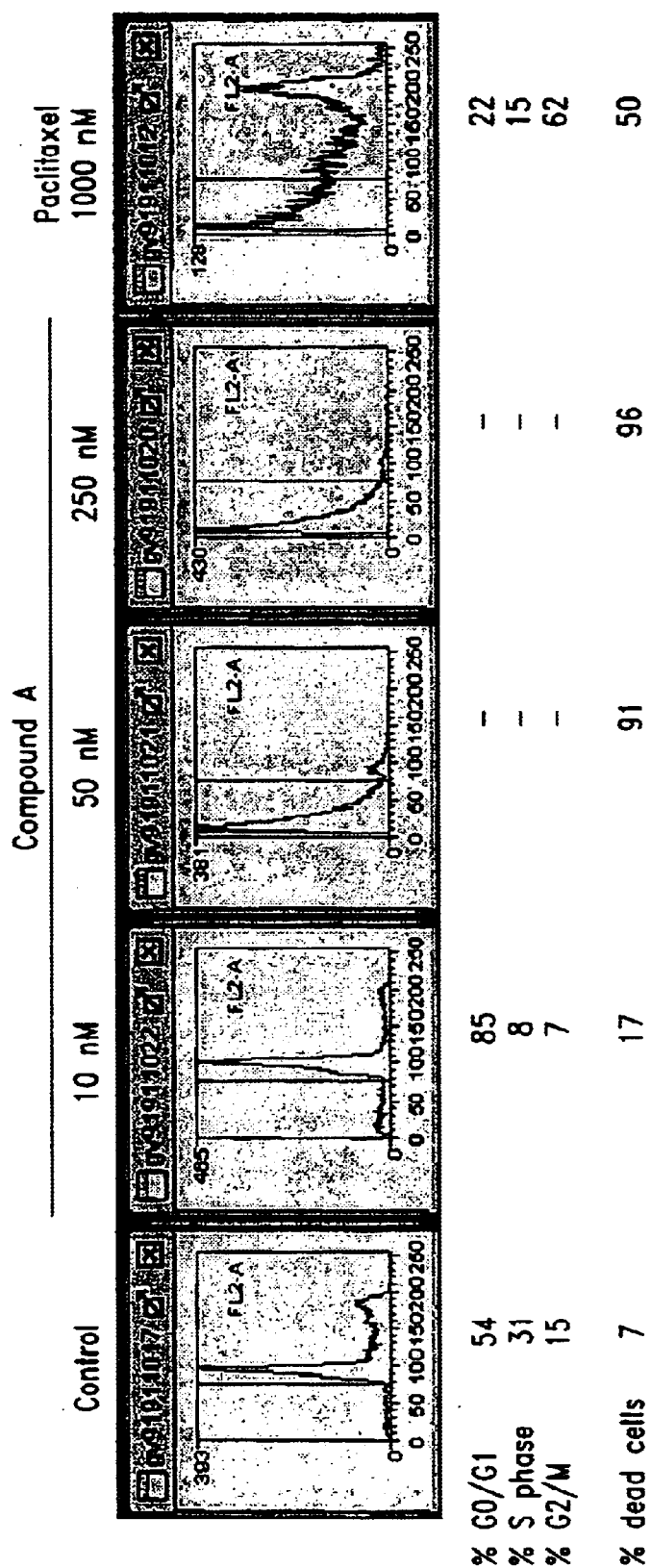

FIG. 2: Effects of Compound A on Cell Cycle Progression and Viability of THP-1 Cells.

THP-1 cells were cultured for 2 days with the indicated concentration of Compound A or 1000 nM paclitaxel then collected and fixed in 70% ethanol prior to staining with propidium iodide and DNA content determined by flow cytometry. The numbers indicate the % of cells in the various cell cycle phases relative to all cells with ≧2N DNA content and also the % dead cells (ie. subdiploid≦2N cells) to the left of the marker (the vertical line) that arose during the culture period.

Figure 3:
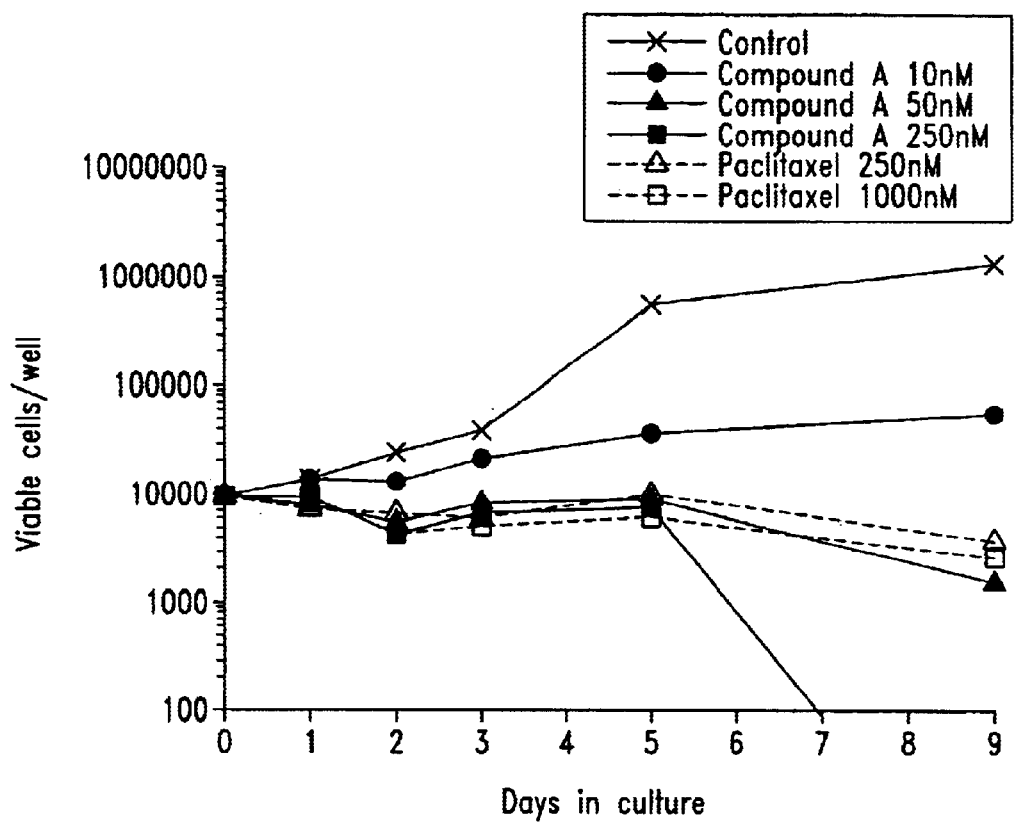

FIG. 3: Effects of Compound A on the proliferation of A549 cells.

A549 cells were seeded at ~10,000 cells/well and cultured in the presence of the indicted concentrations of Compound A or paclitaxel. Cells were collected and the viable cell number determined by haemocytometer counting of trypan blue stained cells at the various times. The results are the averages ±SEM of triplicate cultures.

Figure 4:
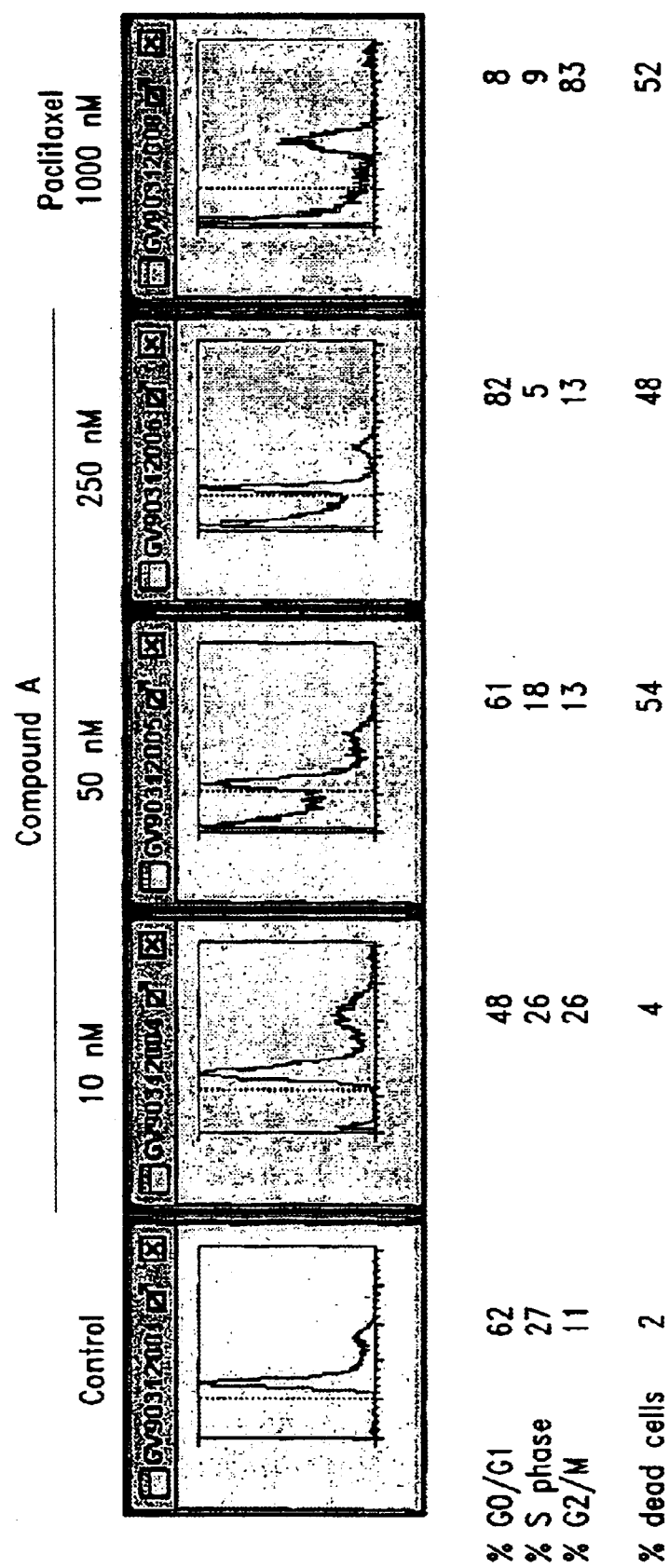

FIG. 4: Effects of Compound A on Cell Cycle Progression and Viability of A549 Cells.

A549 cells were cultured for 6 days with the indicated concentration of Compound A or 1 μM paclitaxel then collected and fixed in 70% ethanol prior to staining with propidium iodide and DNA content determined by flow cytometry. The numbers indicate the % of cells in the various cell cycle phases relative to all cells with ≧2N DNA content and also the % dead cells (ie. subdiploid≦2N cells) to the left of the marker that arose during the culture period.

Figure 5A:
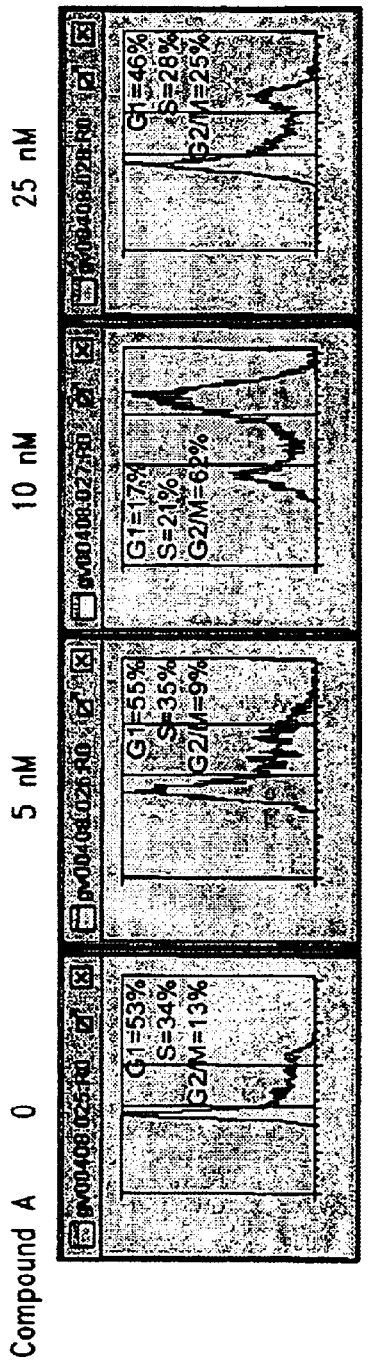
Figure 5B:
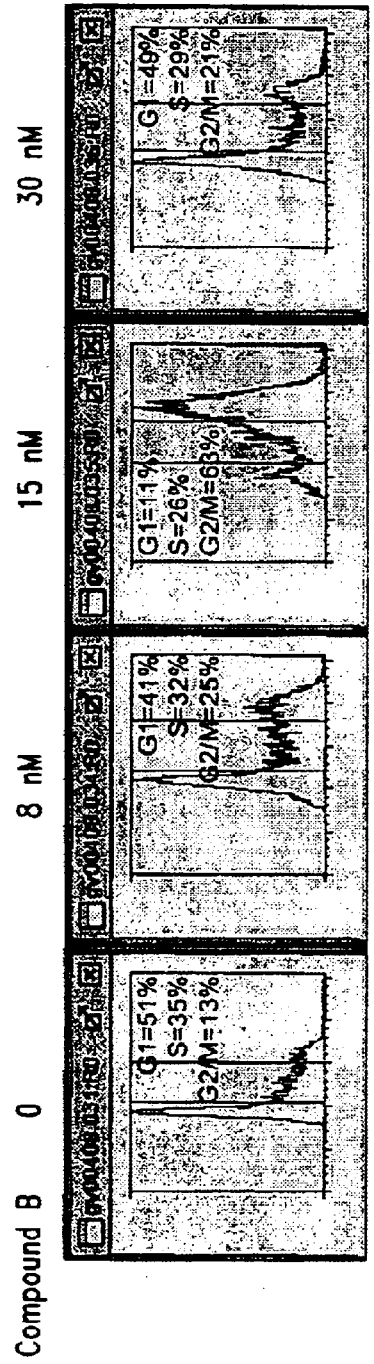

FIG. 5: Compounds A and B Induce G2/M Phase Accumulation of K362 Leukemic Cells

K562 cells were cultured for 3 days with the indicated concentration of Compounds A or B then collected and fixed in 70% ethanol prior to staining with propidium iodide and DNA content determined by flow cytometry. The numbers indicate the % of cells in G0/G1, S and G2/M phases of the cell cycle respectively relative to all cells with ≧2N DNA content.

Figure 6:
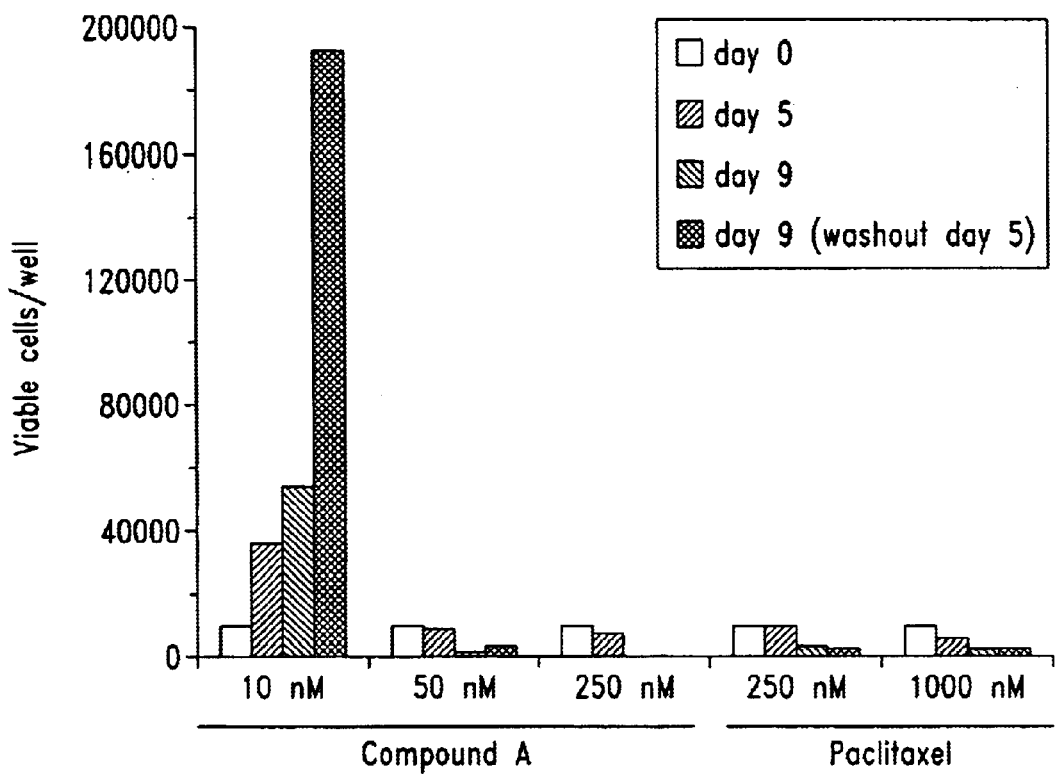

FIG. 6: Cytostatic Effects of Compound A on A549 Cells are Reversible

A549 cells were seeded at ~10,000 cells/well and cultured in the presence of the indicted concentrations of Compound A or paclitaxel and the viable cell numbers determined by haemocytometer counting of trypan blue stained cells at the various times. On day 5 some of the cells were washed, resuspended in fresh medium lacking the various treatments and cultured for another 4 days prior to counting.

Figure 7A:
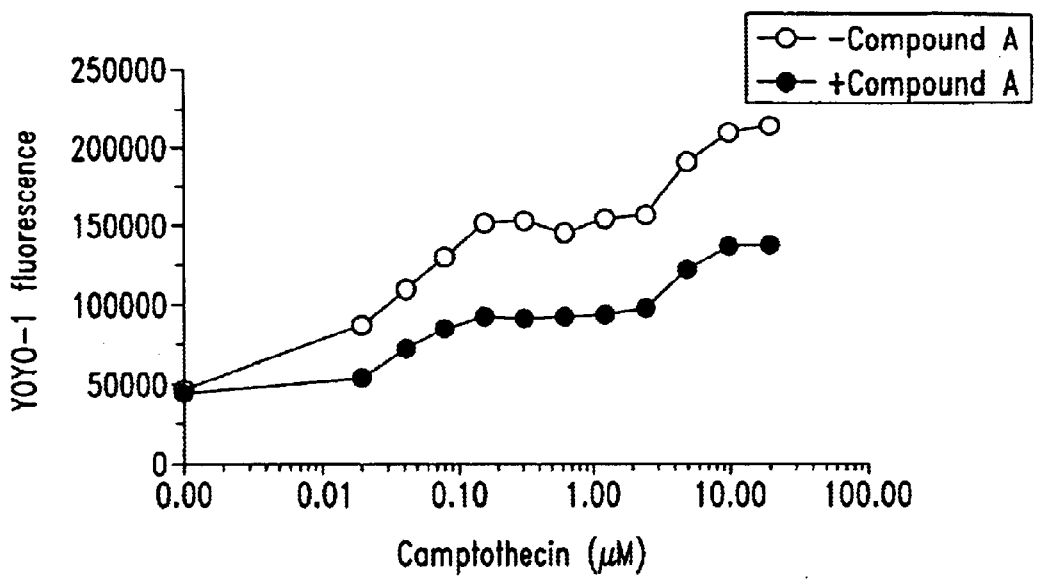
Figure 7B:
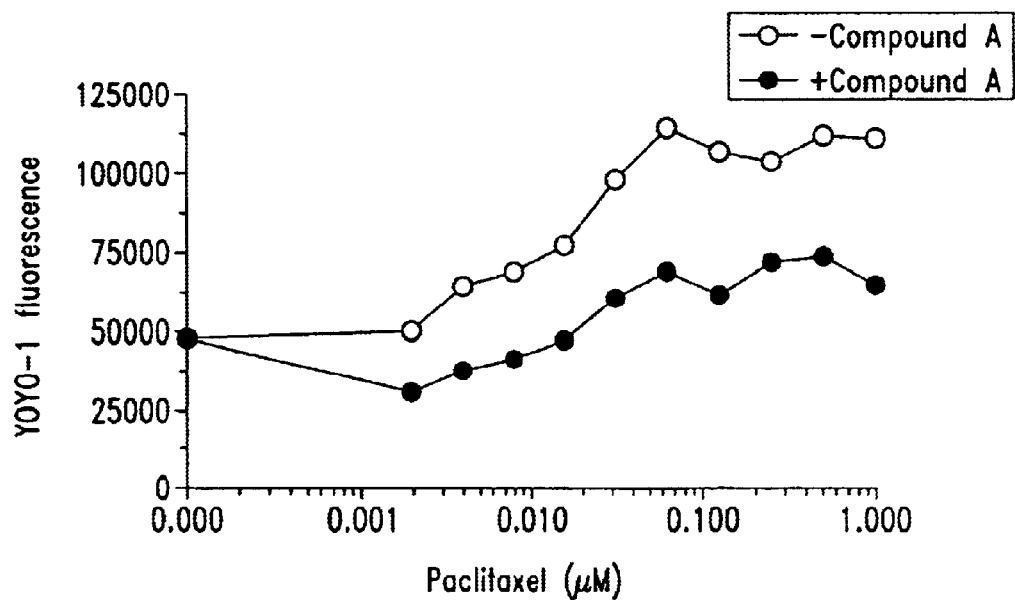

FIG. 7: Compound A Inhibits Camptothecin- and Paclitaxel-Induced Cytotoxicity of A549 Cells A549 cells in 96 well plates were cultured for 3 days in the presence or absence of 10 nM Compound A together with the indicated concentrations of (A) camptothecin or (B) paclitaxel. Loss of membrane integrity was then assessed by the addition of the fluorescent DNA-binding dye YOYO-1 and the increased fluorescence accompanying cell death measured using a fluorescent plate reader.

Figure 8:
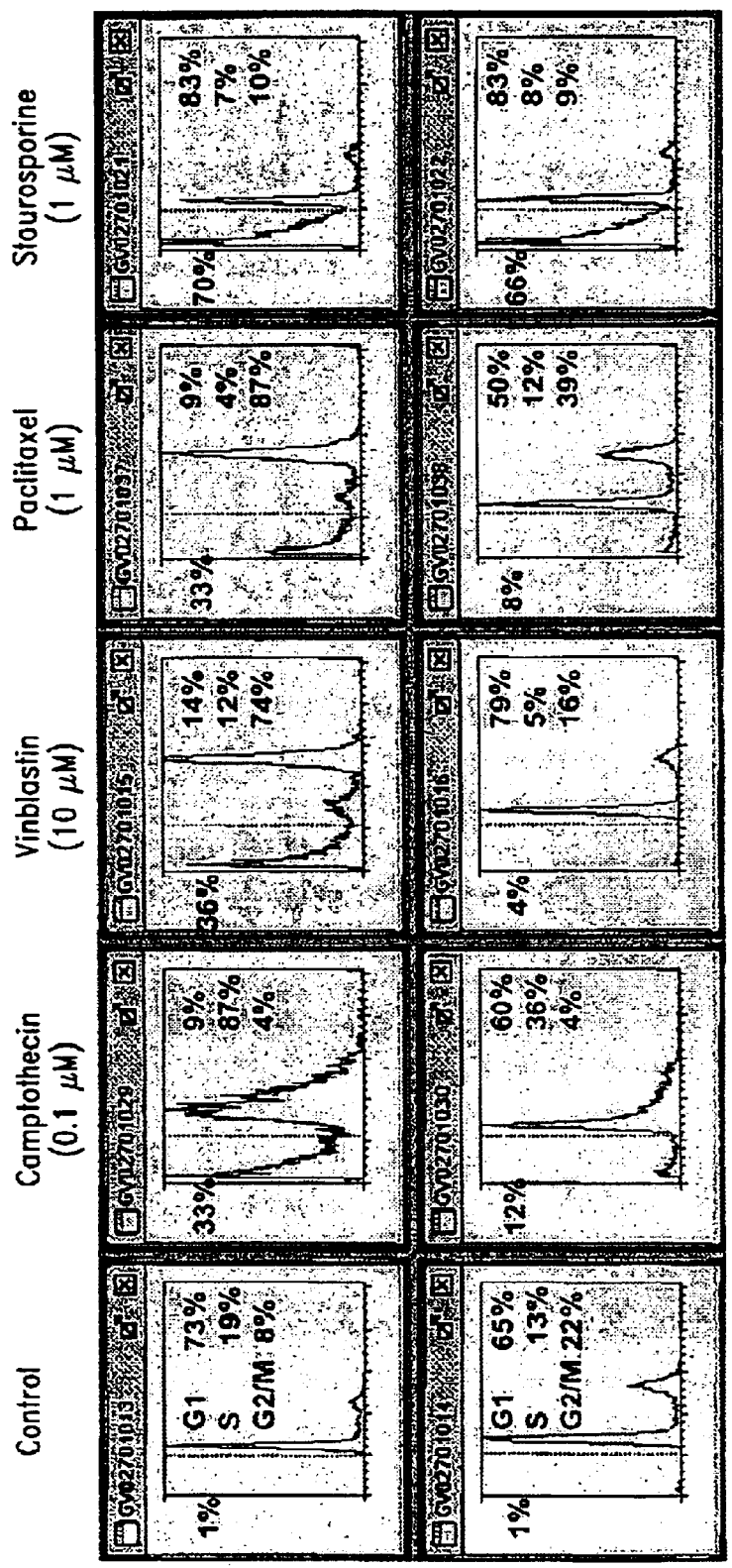

FIG. 8: Compound A Inhibits Cell Cycle Arrest and Cell Death Induced by Anti-Cancer Agents but not by Staurosporine A549 cells in 6 well plates were cultured for 3 days in the presence or absence of 10 nM Compound A together with 0.1 μM camptothecin, 10 μM vinblastin, 1 μM paclitaxel or 1 μM staurosporine as indicated. The cells were then collected and fixed in 70% ethanol prior to staining with propidium iodide and DNA content determined by flow cytometry. The numbers indicate the % of cells in the various cell cycle phases relative to all cells with ≧2N DNA content and also the % dead cells (ie. subdiploid ≦2N cells) to the left of the dotted marker that arose during the culture period.

FIG. 9: Compound A Does not Induce Senescence-Associated β-Galactosidase Activity in A549 Cells A549 cells were seeded at 10,000 cell/well in 6 well plates in the presence or absence of varying concentrations of Compound A (10–50 nM) or 250 nM doxorubicin for 10 days prior to their processing and staining overnight for senescence-associated β-galactosidase activity as described previously (Dimri et al., 1995, *Proc Natl Acad Sci USA* 1995 92(20):9363–7). For Compound A only the 10 nM treatment is shown but there was no detectable SA-β gal activity at any other concentrations tested. PC, phase contrast microscopy. BF, bright field microscopy Magnification×200.

FIG. 10: Compound A Inhibits Growth of Human Tumour Cells in a Mouse Xenograft Model Athymic Balb/c nude mice (Rygard and Povisen, 1969, *Acta Pathol Microbiol Scand*, 77: 758) were inoculated subcutaneously in the dorsal flank with $2 \times 10^6$ PC3 cells. Compound A was administered (3 mg/kg) after eight days when the tumours became palpable by intraperitoneal injection three times a week. Compound A was first solubilized in ethanol then mixed 1:1 with cremaphore and diluted in saline for injection. Control animals were treated in an analogous manner with the same vehicle but lacking Compound A. (A) Effect of Compound A on mean tumour volume. Tumour volumes were measured using a micrometer caliper at the indicated times. The data represents mean tumour volume ±SEM (B) Effect of Compound A on mean tumour mass. At the end of the experiment (29 days post inoculation of PC3 cells) the mice were sacrificed, the tumours excised and then weighed. The data represents mean tumour weight ±SEM.

DETAILED DESCRIPTION OF THE INVENTION

Cyclopenta[b]benzofurans previously reported carry a methoxy group or similar small substituent (Greger et al, 2001, *Phytochemistry*, 57, (1); 57–64) at the 6- or 8-positions. In contrast, the compounds of the present invention carry a sterically bulky group at the 6-oxy-position, in particular, a dioxanyl group. The dioxanyl group of Formula (ii) (depicted below as sub-Formula (a)) has not previously been reported from a natural source. Without intending to limit the invention by theory, it is believed that the presence at the 6-oxy-position of a sterically bulky group, ie spatially larger than a methoxy group, may confer both cytotoxic and cytostatic properties on the compounds having a cyclopenta[b]benzofuran core.

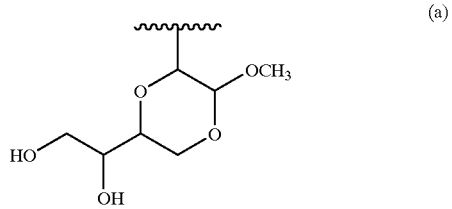

(a)

The invention includes within its scope pharmaceutically acceptable salts, derivatives, or prodrugs of compounds of Formula (I), particularly of Formula (i), such as Compounds A and B.

The term "salt, or prodrug" includes any pharmaceutically acceptable salt, ester, glycoside, solvate, hydrate or any other compound which, upon administration to the recipient subject is capable of providing (directly or indirectly, for example, by chemical or in vivo enzymatic or hydrolytic degradation) a compound of the invention as described herein.

Suitable pharmaceutically acceptable salts include salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids. Base salts include, but are not limited to those formed with pharmaceutically acceptable cations, such as sodium, potassium, lithium, calcium, magnesium, ammonium and alkylammonium.

The preparation of salts can be carried out by methods known in the art. It will also be appreciated that non-pharmaceutically acceptable salts also fall within the scope of the invention, since these may be useful as intermediates in the preparation of pharmaceutically acceptable salts.

The compounds of the invention may be in crystalline form or as a solvate (e.g., hydrates). Methods of solvation will be known to those skilled in the art.

Prodrugs of compounds of formula (I) are also within the scope of the invention. The term "prodrug" includes derivatives that are converted its vivo to the compounds of the invention and include for example, ester (eg acetate) and glycoside derivatives of free hydroxy groups, which may undergo in vivo degradation to release a compound of the invention. Other suitable prodrugs may include esters of free carboxylic acid groups. The preparation of suitable prodrugs is further described in *Design of Prodrugs*, H. Bundgaard, Elseveir, 1985, the contents of which is incorporated by reference.

It will also be recognised that certain Y groups of Formula (I), in particular the dioxanyl groups of compounds as depicted in Formula (i) and (ii), may possess asymmetric centres and are therefore capable of existing in more than one stereoisomeric form. The invention thus also relates to compounds in substantially pure isomeric form at one or more asymmetric (chiral) centres eg., greater than about 90% ee, such as about 95% or 97% ee, preferably greater than 99% ee, as well as mixtures, including racemic mixtures, thereof. Such isomers may be resolved by conventional methods, eg, chromatography, or use of a resolving agent. The present invention thus provides Compounds A and B.

As used herein, the term "alkyl", when used alone or in compound words such as "arylalkyl" refers to a straight chain, branched or cyclic hydrocarbon group, preferably $C_{1-20}$, such as $C_{1-10}$. The term "$C_1$–$C_6$ alkyl" refers to a straight chain, branched or cyclic alkyl group of 1 to 6 carbon atoms. Examples of "$C_{1-6}$ alkyl" include methyl, ethyl, iso-propyl, n-propyl, n-butyl, sec-butyl, t-butyl, n-pentyl, isopentyl, 2,2-dimethypropyl, n-hexyl, 2-methylpentyl, 2,2-dimethylbutyl, 3-methylpentyl and 2,3-dimethylbutyl. Examples of cyclic $C_{1-6}$ alkyl include cyclopropyl, cyclobutyl, cyclopentyl and cyclohexyl. Other examples of alkyl include: heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. An alkyl group may be optionally substituted by one or more optional substituents as herein defined. Optionally, the straight, branched or cyclic hydrocarbon group (having at least 2 carbon atoms) may contain one, two or more degrees of unsaturation so as to form an alkenyl or alkynyl group, preferably a $C_{2-20}$ alkenyl, more preferably a $C_{2-6}$ alkenyl, or a $C_{2-20}$ alkynyl, more preferably a $C_{2-6}$ alkynyl. Examples thereof include a hydrocarbon residue containing one or two or more double bonds, or one or two or more triple bonds. Thus, "alkyl" is taken to include alkenyl and alkynyl.

The term "aryl", when used alone or in compound words such as "arylalkyl", denotes single, polynuclear, conjugated or fused residues of aromatic hydrocarbons or aromatic heterocyclic (heteroaryl) ring systems, wherein one or more carbon atoms of a cyclic hydrocarbon residue is substituted with a heteroatom to provide an aromatic residue. Where two or more carbon atoms are replaced, this may be by two or more of the same heteroatom or by different heteroatoms. Suitable heteroatoms include O, N, S and Se.

Examples of "aryl" include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl, pyridyl, 4-phenylpyridyl, 3-phenylpyridyl, thienyl, furyl, pyrrolyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benoxazolyl, benzothiazolyl and the like. Preferred hydrocarbon aryl groups include phenyl and naphthyl. Preferred heterocyclic aryl groups include pyridyl, thienyl, furyl, pyrrolyl An aryl group may be optionally substituted by one or more optional substituents as herein defined.

The term "acyl" refers to a group —C(O)—R wherein R is any carbon containing moiety such as an optionally alkyl or substituted aryl group. Examples of acyl include straight chain or branched alkanoyl such as, acetyl, propanoyl, butanoyl, 2-methylpropanoyl, pentanoyl, 2,2-dimethylpropanyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl, such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]. Since the R group may be optionally substituted as described above, "acyl" is taken to refer to optionally substituted acyl.

Optional substituents for alkyl, aryl or acyl include halo (bromo, fluoro, chloro, iodo), hydroxy, $C_{1-6}$alkyl (eg methyl, ethyl, propyl (n- and i- isomers)), $C_{1-6}$alkoxy (eg methoxy, ethoxy, propoxy (n- and i- isomers), butoxy (n-, sec- and t-isomers), nitro, amino, $C_{1-6}$alkylamino (eg methyl amino, ethyl amino, propyl (n- and i- isomers)amino), $C_{1-6}$dialkylamino (eg dimethylamino, diethylamino, diisopropylamino), halomethyl (eg trifluoromethyl, tribromomethyl, trichloromethyl), halomethoxy (eg trifluoromethoxy, tribromomethoxy, trichloromethoxy) and acetyl. Furthermore, optional substituents for Y (phenyl, benzyl, benzoyl, $C_3$–$C_8$ cycloalkyl, $CH_2$-($C_3$–$C_8$ cycloalkyl), 5–6 membered-heterocyclyl and $CH_2$-(5–6 membered-heterocyclyl)) include, as well as the substituents above, alkyl substituted with one or more of hydroxy $C_{1-6}$alkyloxy, $C_{1-6}$acyloxy, aryloxy, aryl$C_{1-6}$alkyloxy, $C_{1-6}$cycloalkyl$C_{1-6}$alkyloxy, aryl$C_{1-6}$acyloxy, $C_{1-6}$cycloalkyl$C_{1-6}$acyloxy and C1-linked saccharidoxy.

The term "arylalkyl" and "cycloalkylalkyl" refer to an alkyl group (preferably straight chain) substituted (preferably terminally) by an aryl and a cycloalkyl group, respectively. Similarly, the terms "arylacyl" and "cycloalkylacyl" refer to an acyl group (preferably where R is straight chain alkyl) substituted (for example, terminally substituted) by an aryl and a cycloalkyl group, respectively Preferred C-1 linked saccharides are a furanose or pyranose saccharide (sugar) substituent which is linked to the backbone structure shown in Formula (I) through the saccharides's 1-carbon (conventional chemical numbering) to form an acetal at any one of positions $R_1$, $R_2$, $R_3$, $R_4$, $R_5$, $R_6$, or $R_7$ or an ester linkage at the $R_8$ or an amide at $R_9$ or $R_{10}$ position. Exemplary saccharide groups include reducing sugars such as glucose, ribose, arabinose, xylose, mannose and galactoses, each being linked to an oxygen atom of the structure of Formula (I) through the C-1 carbon of the saccharide group.

A 5–6 membered heterocyclyl group includes aromatic 5–6-membered heterocyclic aryl groups (heteroaryl) as described above and non aromatic 5–6-membered heterocyclic groups containing one or more heteroatoms (preferably 1 or 2) independently selected from O, N, S and Se. Examples thereof include dioxanyl, pyranyl, tetrahydrofuranyl, piperidyl, morpholino, piperazinyl, thiomorpholino and saccharides, for example, those described above.

In one embodiment of Formula (I) or Formula (i) of the invention, each of $R^4$–$R^7$ and $R^1$–$R^7$ respectively may independently be selected from the group consisting of hydrogen, methyl, ethyl, n-propyl, i-propyl, n-butyl, sec-butyl, t-butyl, cyclopropylmethyl (or cyclopropylethyl), cyclobutylmethyl (or -ethyl), cyclopentylmethyl (or -ethyl), cyclohexylmethyl (or -ethyl), phenyl, benzyl, acetyl and C-1 linked saccharide.

In another embodiment of Formula (I), (i) or (ii) of the invention, $R^8$ of X=$OR^8$ is selected from the group of hydrogen, $C_{1-6}$ alkyl, phenyl, benzyl and C-1 linked saccharide.

In another embodiment of Formula (I), (i) or (ii) of the invention $R^9$ and $R^{10}$ of X=$NR^9R^{10}$ are independently selected from hydrogen, $C_{1-6}$ alkyl, phenyl or benzyl.

The derivatisation of hydroxy groups of Compounds A and B to form compounds of Formula (i), (ie where any one of $R^1$–$R^7$ is not hydrogen) can be carried out by methods known in the art for alkylating, arylating or acylating hydroxy groups, for example as described in *Protective Groups in Organic Synthesis* T. W. Greene and P. G. M. Wutz, (1999) Wiley Interscience, New York, and *Advanced Organic Chemisty*, J. March, ($4^{th}$ Edition), Wiley-InterScience (the entire contents of which are incorporated herein by reference). For example, hydroxy groups can be alkylated using alkyl halides such as methyl iodide or dialkyl sulfates such as dimethyl and diethyl sulfate. Acylation can be effected by treatment with appropriate carboxylic acids, acid halides or acid anhydrides in the presence of a base or coupling agent. Benzylation may be effected by treatment with a benzyl halide compound such as benzyl bromide, chloride or iodide. De-esterification of the methyl ester can be effected by treatment of the ester with aqueous base. Esterification of a carboxylic acid can be achieved by conventional means including treatment with an appropriate alcohol in the presence of acid, or treatment with alkyl sulfates or alkyl halides.

Glycosidic formation may be effected chemically, eg by reacting the starting compound with a protected sugar compound in which C-1 has been activated by halogenation for coupling with the hydroxyl or carboxyl groups and the sugar hydroxyls have been blocked by protecting groups. Alternatively, glycoside formation may be effected enzymatically using an appropriate glycosyltransferase such as UDP-galactose dependent galactocyltransferase and UDP-glucose dependent glycocyltransferase (SIGMA).

The skilled person will recognise that in order to selectively install any one or more of the $R^1$–$R^{10}$ groups as defined herein (eg where $R^1$–$R^7$ are not hydrogen), this may require the judicious protection and/or deprotection, of one or more of the oxy and/or carboxy groups. Selective derivatisation of one or more hydroxy or carboxy groups may be achieved via conventional techniques by the use of protecting groups with different degrees of stability under appropriate conditions.

Methods for the conversion of a carboxylic acid or ester group; ie. where X is $OR^8$ to an amide (X is $NR^9R^{10}$) are known to the skilled person and may include treatment of a carboxylic acid with an appropriate amine in the presence of a coupling reagent such as DCC or treatment of an acid halide with the appropriate amine. Other methods which may be suitable are described in Larock, R. E, *Comprehensive Organic Transformations* pp 963–995, VCH Publishers (1989).

As used herein, the term "protecting group", refers to an introduced functionality which may temporarily render a particular functional group, eg hydroxy or carboxylic acid, inactive under certain conditions in which the group might otherwise be reactive. Suitable protecting groups are known to those skilled in the art, for example as described in *Protective Groups in Organic Synthesis* (supra). Suitable protecting groups for hydroxy include alkyl, (such as $C_1$–$C_6$alkyl), acyl (such as $C(O)C_1$–$C_6$alkyl, benzoyl and the like), benzyl, and silyl groups (such as trimethylsilyl, t-butyldimethyl silyl, t-butyldiphlenylsilyl and the like). Other suitable groups for hydroxy substituents and a carboxy substituent (acid, amide etc) can be found within Greene supra. The stability of various groups under certain conditions is understood by the skilled person and is further exemplified in *Protective Groups in Organic Synthesis* (supra).

It will be appreciated that these protected compounds may be useful as intermediates in the preparation of certain compounds of Formula (I) and therefore, these also form a further aspect of the invention.

It will also be recognised that some groups, eg alkyl, acyl or arylalkyl, (such as methyl, ethyl, propyl, acetyl, benzyl etc) may serve as either a temporary protecting group or as a non-hydrogen $R^1$–$R^8$ group in Formula (I).

The dioxanyl group may be cleaved from the 6-oxy position of the cyclopentabenzofuran core using known methods to afford a dioxane compound. The resulting dioxane compound could be used to substitute other compounds, such as oxy-substituted compounds, including the corresponding 6-oxy position, or other oxy positions, on other cyclopentabenzofuran compounds such as those described in the references herein.

It will also be understood that cyclopentabenzofuran compounds, having a methoxy substituent at the 6-position, such as those described in the references cited herein (incorporated herein by reference) eg Reference Compounds 1–3 (as described in Example 4), can, where appropriate be 6-demethylated, and the resulting 6-hydroxy group reacted with a suitable Y precursor to form an 6-OY group. Methods therefor are known in the art, for example, one method may involve reacting the 6-OH group with a Y-halogen compound where halogen includes Cl, Br and I. Alternatively, access to the cyclopentabenzofuran core, incorporation of the Y group can be achieved via synthetic methods analogous to that described in Trost et al, *J. Am. Chem. Soc.,* 1990, 112, 9022–9024. Such 6-OY compounds form a further aspect of the invention.

In some preferred embodiments of the present invention, one or more of the following definitions apply:

$R^1$ and $R^2$ are both hydrogen.

$R^1$ and $R^2$ are hydrogen, and $R^3$ is methyl.

at least one of $R^3$–$R^5$ is methyl, ethyl or propyl, preferably methyl.

at least two of $R^3$–$R^5$ are methyl, ethyl or propyl, preferably methyl.

all of $R^3$–$R^5$ are methyl, ethyl or propyl, preferably methyl.

$R^6$ and $R^7$ are both hydrogen.

at least one of $R^{11}$ and $R^{12}$ is hydrogen, preferably $R^{11}$ and $R^{12}$ are both hydrogen.

X is $OR^8$ where $R^8$ is selected from hydrogen, methyl, ethyl or propyl, preferably, methyl.

X is $NR^9R^{10}$ where $R^9$ and $R^{10}$ are both hydrogen or methyl; or $R^9$ and $R^{10}$ are different but at least one of $R^9$ or $R^{10}$ is hydrogen and the other is $C_{1-6}$ alkyl, such as methyl, ethyl or propyl.

Y is an optionally substituted 5–6 membered heterocyclyl group or an optionally substituted $C_5$–$C_6$ cycloalkyl group.

Particularly preferred forms of Formula (ii) are Compounds A and B.

The compounds of the invention may have use in the treatment of cancerous conditions, or other conditions associated with cellular hyperproliferation, in a subject. Subjects which may be treated by the compounds of the invention include mammals, for example, humans, primates, livestock animals (eg. sheep, cows, horses, goats, pigs), companion animals, (eg. dogs, cats, rabbits, guinea pigs), laboratory test animals, (eg, rats, mice, guinea pigs, dogs, rabbits, primates) or captured wild animals. Most preferably, humans are the subjects to be treated.

As used herein the term "treatment" is intended to include the prevention, slowing, interruption or halting of the growth of a cancer, tumour or hyperproliferative cell, or a reduction in the number of targeted cells (or size of the growth mass) or the total destruction of said cell, wherein said cells are cancer, tumour or hyperproliferative cells.

Cancerous conditions which may be treated by the compounds of the present invention include conditions wherein the cancers or tumours may be simple (monoclonal, ie composed of a single neoplastic cell type), mixed (polyclonal, ie. composed of more than one neoplastic cell type) or compound (ie. composed of more than one neoplastic cell type and derived from more than one germ layer) and may include benign and malignant neoplasia/hyperplasia. Some examples of cancerous conditions which may be treated by the present invention include leukemia and breast, colon, bladder, pancreatic, endometrial, head and neck, mesothelioma, myeloma, oesophagal/oral, testicular, thyroid, uterine, prostate, renal, lung, ovarian, cervical brain, skin, liver, bone, bowel and stomach cancers, sarcomas, tumours and melanomas. Examples of benign hyperplasias include those of vascular (eg hemangioma), prostate, renal, adrenal, hepatic, colon (eg colonic crypt), parathyroid gland and other tissues.

As the compounds of the invention may have cytostatic as well as cytotoxic properties, they may also have potential use as therapeutic agents in the suppression of the growth of target populations of cells other than cancer or tumour cells, for example disease states or conditions associated with cellular hyperproliferation. Such conditions may include atherosclerosis and restinosis (neointimal hyperplasia) and hyperproliferation due to or accompanying an inflammatory response, eg arthritis, (including rheumatoid arthritis, osteoarthritis and inflammatory arthritis), psoriasis and periodontal disease, or cellular hyperproliferation due to the viral infection of cells such as human papilloma virus.

The compounds of the invention, eg Compounds A and B, may be used in therapy in conjunction with other therapeutic compounds, such as anti-cancer compounds, including paclitaxel, camptothecin, vinblastin and doxorubicin.

Thus, another aspect of the invention relates to a method for the treatment of cancer or a cancerous condition comprising the administration of an effective amount of a compound of Formula (I) and a further therapeutic agent to a subject in need thereof, and the use of said compound in the manufacture of a medicament for use in conjunction with other therapeutic agents.

The compounds of the invention and the further therapeutic agent may be administered simultaneously, as a single composition or as discrete compositions, or may be administered separately, ie, one after the other at suitable intervals as determined by the attending physician. Thus, the invention also provides a kit comprising a compound of Formula (I) together with a further therapeutic agent.

As used herein, the term "effective amount" of a compound relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 $\mu$g to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 $\mu$g to 100 mg per kg of body weight per dosage, such as up to 50 mg per kg body weight per dosage. The dosing regime for each subject may be dependent upon the age, weight, health and medical history of the subject and the extent and progress of the condition to be treated, and can be determined by the attending physician.

The active ingredient may be administered in a single dose or a series of doses. While it is possible for the active ingredient to be administered alone, it is preferable to present it as a composition, preferably as a pharmaceutical composition.

The carrier must be pharmaceutically acceptable in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules optionally mixed with a binder (e.g inert diluent, preservative disintegrant such as sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for rectal administration may be presented as a suppository with a suitable base comprising, for example, cocoa butter, gelatin, polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose scaled containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants may include magnesium stearate, stearic acid, sodium oleate, sodium chloride or talc. Suitable time delay agents may include glyceryl monostearate or glyceryl distearate.

One or more embodiments of the present invention may also provide methods, compositions agents or compounds which have an advantage over (or avoid a disadvantage) associated with known methods, compositions, agents or compounds used in the chemotherapeutic treatment of cancerous conditions or conditions associated with the hyperproliferation of cells. Such advantages may include one or more of: increased therapeutic activity, reduced side effects, reduced cytotoxicity to non-cancerous or non-proliferative cells, improved solubility or dispersibilty for formulation into pharmaceutical compositions, improved stability or a more readily available means of obtaining said compounds, eg. by simpler, cheaper or higher yielding synthetic or isolation processes.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The references and citations disclosed within this specification are taken to be incorporated herein in their entirety.

The invention will now be described with reference to the following Examples which are included for the purpose of illustrating embodiments of the invention and not to be construed as limiting the generality hereinbefore described.

EXAMPLES

Example 1

Isolation of Compounds A and B from Aglaia Leptantha

Compounds A and B were isolated using the following procedure:

(a) Treat a sample of ground bark from the tree species Aglaia leptantha with methanol.

(b) Filter the extract and concentrate the resulting solution under vacuum.

(c) Fractionate the extract via solid-phase extraction on a C-18 Varian extraction column (10 g) using 0.1% formic acid in acetonitrile/water with increasing acetonitrile concentrations.

(d) Collect the eluate obtained with an acetonitrile/water ratio of 7:20. Compounds A and B have a UV absorption maximum of 200, 273 run (acetonitrile/water/0.1% formic acid) and a HPLC retention times of approximately 30.67 (Compound A) and 31.05 minutes (Compound B) under the following conditions:

C-8 Symmetry column (WATERS), 4.6×250 mm, 5 μm, 1 mL/min, linear gradient from 0% to 90% acetonitrile in water in 40 minutes with 0.1% formic acid.

(e) Concentrate fraction obtained under step (d).

(f) Chromatograph the concentrate obtained under step (e) on a C-18 preparative column (WATERS, Nova-Pak C-18, 6 micron, 2.5×25 cm) at a flow rate of 20 mL/min using a linear gradient from 25% to 45% acetonitrile in water in 30 minutes with 0.1%

(g) Collect and concentrate the eluates with the chromatographic and spectroscopic characteristics outlined in step (d) at approximately 22 minutes.

(h) Chromatograph each eluate obtained under (g) on a Sephadex LH20 column using methanol as a solvent. Collect and concentrate the fractions with spectral characteristics outlined in (d). These samples were used for the structural elucidation of Compounds A and B.

(i) Alternatively to steps (b), (c) and (d), the methanol extract obtained under (a) may be partitioned with equal volumes of water and dichloromethane. The dichloromethane phase is then processed according to steps (e) to (h).

The compounds thus obtained have the following spectroscopic and physical characteristics;

UV/V is absorption maxima: 223, 275 nm (in MeCN/$H_2O$, 0.1% HCOOH).

MS; Mass spectra were obtained on a Finnigan LCQ iontrap mass spectrometer using the ESI source in the positive ion mode. The sample was dissolved in 0.1%FA in MeOH and introduced into the source by infusion with a syringe pump at rate of 3 μL/min. For Compounds A, signals were observed at m/z 677 $[M+Na]^+$; $MS^2$ yielded m/z 659 $[M+Na-H_2O]^+$; $MS^3$ yielded m/z 627 (loss of 32 amu); $MS^4$ yielded m/z 595 (loss of another 32 amu) and m/z 451 (loss of 176 amu, equivalent to the dioxane sidechain). For compound B signals were observed in the positive ion mode at m/z 677.2 $[M+Na]^4$; $MS^2$ yielded product ions at m/z 627.2 and m/z 659.2. Further fragmentation of the signal at m/z 627.2 yielded a product ion at m/z 595.3.

Accurate mass spectra for Compound A were obtained on the Bruker 47c Fourier Transform-Ion Cyclotron Resonance Mass Spectrometer (FTMS) fitted with an Analytica Electrospray Source (ESI). The sample was dissolved in MeOH and introduced in to the source by direct infusion with a syringe pump at a rate of 60 μL/min. The source was operated with capillary voltage of 100 v. One signal was observed at m/z 677.2194 $[M+Na]^+$ meas.; $C_{34}H_{38}O_{13}Na^+$ requires 677.2204.

NMR

The NMR spectra of Compounds A and B (see Formula (ii) below) were acquired on 400 and 500 MHz Varian INOVA NMR spectrometers, in $CD_3OD$ and $CDCl_3$, respectively. The following experiments were conducted: $^1H$, $^{13}C$, DEPT, HMQC, HMBC, COSY. The $^1H$ NMR chemical shifts (obtained in $CDCl_3$) and the $^{13}C$ NMR chemical shifts are listed in Table 1.

TABLE 1

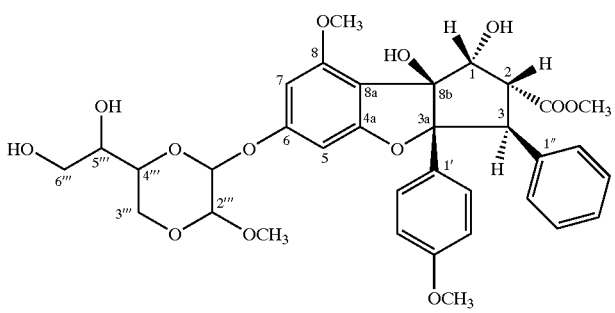

(i)

Compounds A and B
$^1$H and $^{13}$CNMR shifts for Compounds A and B (Preliminary Position Assignments)

| Position Assignments | | Compound A 1H NMR (ppm) | $^{13}$C NMR (ppm) | Compound B $^1$ H NMR (ppm) | $^{13}$C NMR (ppm) |
|---|---|---|---|---|---|
| 1 | CH | 5.03, d, 6.7 Hz, 1H | 79.6 | 5.04, d, 6.8 Hz, 1H | 79.8 |
| 2 | CH | 3.89. dd, 14.2, 6.7 Hz, 1H | 50.03 | 3.9, dd. 14. 6.8 Hz. 1H | 50 |
|  | COOCH$_3$ |  | 170.6 | 170.7 |  |
|  | COOCH$_3$ | 3.65, s, 3H | 52.06 | 3.66, s, 3H | 52 |
| 3 | CH | 4.28, d, 14.2 Hz, 1H | 55.03 | 4.28, d, 14 Hz, 1H | 55 |
| 3a | C |  | 101.9 | 101.8 |  |
| 4a | C |  | 160.6 | 160.2 |  |
| 5 | CH | 6.43. d, 2 Hz, 1H | 92.8 | GAS, d. 2 Hz. 1H | 92.8 |
| 6 | C |  | 160 | 159.8 |  |
|  | OCH$_3$ | 3.87. s, 3H | 55.9 | 3.86, s, 3H | 55.8 |
| 7 | CH | 6.28 d, 2 Hz, 1H | 93.9 | 6.29 d, 2 Hz, 1H | 94.3 |
| 8 | C |  | 157.1 |  | 157.1 |
| 8a | C |  | 109.6 |  | 109.4 |
| 8b | C |  | 93.4 |  |  |
| 1' | C |  | 126.2 |  | 126.2 |
| 2', 6' | 2xCH | 7.10, brd, 9 Hz, 2H | 128.9 | 7.10, brd, 9 Hz, 2H | 128.9 |
| 3', 5' | 2xCH | 6.68, brd, 9 Hz, 2H | 112.7 | 6.69, brd, 9 Hz, 2H | 112.8 |
| 4" | C |  | 158.8 | 158.8 |  |
|  | OCH$_3$ | 3.71, s, 3H | 55.05 | 3.72, s, 3H | 55 |
| 1" | C |  | 136.7 |  | 136.6 |
| 2", 6" | 2xCH | 6.84, m, 2H | 127.8 | 6.86, m, 2H | 127.5 |
| 3", 5" | 2xCH | 7.06, m, 2H | 127.8 | 7.06, m, 2H | 127.5 |
| 4" | CH | 7.06. m, 1H | 126.6 | 7.06, m, 1H | 126.6 |
| 1'" | CH | 5.28, s, 1H | 94 | 5.26, s, 1H | 93.4 |
| 2'" | CH | 4.59, s, 1H | 95.2 | 4.60, s, 1H | 95.2 |
|  | OCH$_3$ | 3.49, s, 3H | 55.1 | 3.5, s, 3H | 55 |
| 3'" | CH$_2$ | 4.13, t, 11.2 Hz, 1H 3.56, dd, 11.7,2 Hz, 1H | 59 | 4.02, t, 11.2 Hz, 1H 3.78. dd, 11.7, 2.4 Hz, 1H | 59.6 |
| 4'" | CH | 4.23, brt, 11.3 Hz, 1H | 68.3 | 4.12, ddd, 11, 6.8, 2.8 Hz, 1H | 67.6 |
| 5'" | CH | 3.61, m. 1H | 70.6 | 3.66, m, 1H | 71.4 |
| 6'" | CH$_2$ | 3.61, m, 2H | 63.3 | 3.61, dd, 10.4, 4.4 Hz, 1H 3.72, m, 1H | 62.5 |

Example 2
Determination of the substitution position of the dioxanyl sidechain on the cyclopentabenzofurane core of Compounds A and B (Acetylation of Compounds A and B)

The objective of this experiment was to unambiguously determine the attachment position of the dioxanyl sidechain to the cyclopentabenzofuran core in Compounds A and B.

Compounds A and B were dissolved in anhydrous pyridine (A: 4.2 mg in 280 μL; B: 3 mg in 400 μL) and acetic anhydride was added (A: 140 μL, B: 200 μL). The reaction mixtures were stirred under an argon atmosphere for 14 (A) and 22 (B) hrs, respectively. The solvents were removed under reduced pressure to afford the diacetates as an orange residue (A 5.8 mg; B: 3 mg). Purification of the crude residues was achieved by silica gel column chromatography eluting with 60% ethylacetate/petrol. The diacetate of Compound A, Compound A' (Formula (iii)), was obtained in 68% yield (3.2 mg), and the diacetate of Compound B, Compound B' (Formula (iii)), was obtained in 41% yield (1.4 mg).

The purity of the two reaction products was assessed by reversed phase HPLC using the same instrumentation as outlined in Example 1 (column: Xterra C-18, 1 mL/min, gradient: from 0 to 100% MeCN in 40 mins). The structures of compounds A' and B' were elucidated by electrospray MS and 1D and 2D NMR experiments using the same conditions as described in Example 1. NMR spectra of Compounds A' and B' were obtained in CDCl$_3$ with 500 and 400 MHz Varian INOVA instruments.

Both compounds yielded a single peak in the HPLC analysis with retention times of 26.3 mins for Compound A', and 27.7 mins for Compound B'. Compounds A' and B' showed positive molecular ions at m/z 761 [M+Na]$^+$ and 1499 [2M+Na]$^+$ indicative of a molecular formula $C_{38}H_{42}O_{15}$. 1 and 2 D NMR experiments ($^1$H, HMQC and HMBC, NOESY) revealed that the two hydroxyl functions on the dioxanyl sidechain were acetylated. The $^1$H and $^{13}$C NMR chemical shifts are summarized in Table 2, and the NOESY spectra in Table 3.

The HMBC experiments of both diacetates show clear correlations of the proton signals of H-5, H-7 and H-1''' to the carbon 6 of the aromatic ring. The proton signals of H-7 and a methoxy group are correlated to the carbon 8. This clearly indicates that the dioxanyl sidechain is attached at the position C-6 of the cyclopentabenzofuran core.

Further support for the position of the dioxanyl sidechain was derived from the NOESY spectra of both compounds. The NOE signals are observed from both H-5 and H-7 to H-1''' of the dioxanyl side chain, and only H-7 shows a NOE signal to the C-8 methoxy signal. The NOE signals observed in the dioxanyl ring systems of the two compounds clearly indicate that they differ in regard to the stereochemistry of the di-hydroxyethane sidechain. The NOE signals for the cyclopentabenzofuran core are in agreement with published data and confirm the stereochemistry depicted in Tables 1 and 2.

TABLE 2

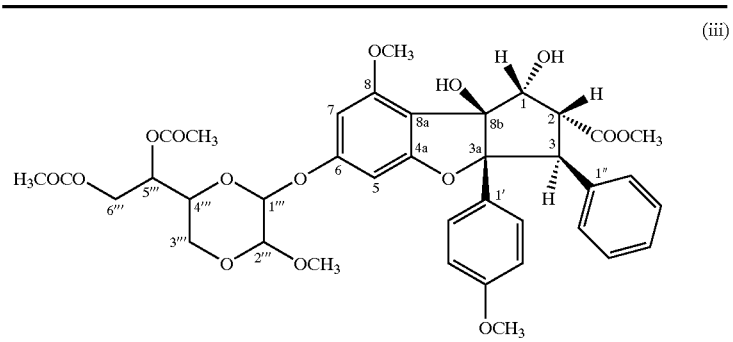

(iii)

Compounds A' and B' (Diacetates of Compounds A and B)
$^1$H and $^{13}$C NMR chemical shifts for Compounds A' and B'

| | | Compound A' (Diacetate of Compound A) | | Compound B' (Diacetate of Compound B) | |
|---|---|---|---|---|---|
| Position | Assignment | $^1$HNMR | $^{13}$C NMR | $^1$H NMR | $^{13}$C NMR |
| 1 | CH | 5.06, d, 8 Hz | 19.8 | 5.07, d, 8 Hz | 79.8 |
| 2 | CH | 3.89, under OCH$_3$-8 | 50.4 | 3.87, under OCH$_3$-8 | 50 |
| 2 | COOCH$_3$ | | 170.4 | | 170.4 |
| 2 | COOCH$_3$ | 3.64, s | 51.9 | 3.63, s | 51.8 |
| 3 | CH | 4.26. d. 14 Hz | 55 | 4.27, d, 14.4 Hz | 54.8 |
| 3a | C | | 101.9 | | 102 |
| 4a | C | | 160.6 | | 160.5 |
| 5 | CH | 5.43, d, 2 Hz | 93.3 | 6.45, d, 2 Hz | 93.2 |
| 6 | C | | 159.6 | | 159.7 |
| 7 | CH | 6.27 d, 2 Hz | 93.2 | 6.29, d, 2 Hz | 93 |
| 8 | C | | 157 | | 156.9 |
| S | OCH$_3$ | 3.89. s | 56 | 3.88, s | 55.8 |
| Ba | C | | 109.8 | | 109.6 |
| Sb | C | | 93.5 | | 93.4 |
| Sb | OH | 2.35,s | | | 223 |
| 1' | C | | 126.2 | | 126.4 |
| 2', 6' | 2xCH | 7.10, brd, 9 Hz | 129.1 | 7.10, brd, 9 Hz | 129 |
| 3', 5' | 2xCH | 6.67, brd, 9 Hz | 112.7 | 6.68, brd, 9 Hz | 112.6 |
| 4' | C | | 158.8 | | 158.6 |
| 4' | OCH$_3$ | 372, s | 55 | 3.72, s | 55 |
| 1" | C | | 136.8 | | 136.6 |
| 2", 6" | 2xCM | 6.83, m | 127.7 | 6.86, m | 127.8 |
| 3", 5" | 2xCH | 7.05,m | 127.1 | 7.05, m | 127.8 |
| 4" | CH | 7.05, m | 126.6 | 7.05, m | 126.6 |
| 1''' | CH | 5.38, s | 93.7 | 5.31, s | 93.2 |
| 2''' | CH | 4.61, s | 95.2 | 4.62, s | 95.2 |
| 2''' | OCH$_3$ | 3.50, s | 55.2 | 3.5, s, 3H | 55 |
| 3''' | CH$_2$ | 3.94, t, 11.2 Hz | 58.8 | 3.93, t, 12 Hz | 59.5 |
| | | 3.54, dd, 11.2, 3 Hz | | 3.59, dd, 12, 2.5 Hz, | |
| 4''' | CH | 4.38, dt, 11, 3 Hz | 66.3 | 4.37, td, 9, 2.5 Hz | 64.9 |
| 5''' | CH | 5.12, td, 6, 3 Hz | 69.1 | 5.00, ddd, 9, 4, 2.5 Hz | 70.2 |
| 6''' | CH$_2$ | 4.22, dd, 11.2, 6 Hz | 61.3 | 4.21, dd, 12.4, 4 Hz, | 61.5 |
| | | 3.88, ? under OCH$_3$-8 | | 4.12, dd, 12.4, 2.5 Hz | |
| 5''' | COCH$_3$ | | 170.3 | | 169.9 |
| 5''' | COCH$_3$ | 2.14, s | 20.8 | 2.07 | 20.8 |
| 6''' | COCH$_3$ | | 170.7 | | 170.8 |
| 6''' | COCH$_3$ | 1.79 | 20.4 | 1.74 | 20.1 |

TABLE 3

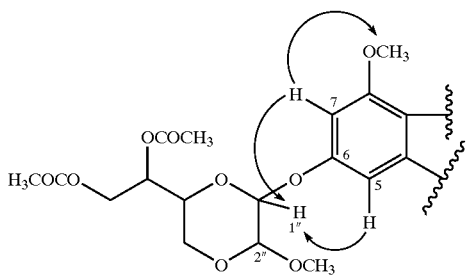

Comparison of NOESY Spectra of Compounds A' and B'

| Compound A' | | Compound B' | |
|---|---|---|---|
| 1H NMR | NOEs | 1H NMR | NOEs |
| 6.43, d, H-5 | 5.38, s, H-1''' | 6.45, d, H-5 | 5.31, s, H-1''' |
|  | 4.38, dt, H-4''' |  | 4.37, td, H-4''' |
|  |  |  | 4.21, dd, H-6'''-1 |
|  |  |  | 1.74, s, $COCH_3$-6''' |
| 6.27, d, H-7 | 5.38, s, H-1''' | 6.29, d, H-7 | 5.31, s, H-1''' |
|  |  |  | 4.21, dd, H-6'''-1 |
|  | 3.89, s, $OCH_3$-8 |  |  |
| 5.38, s, H-1''' | 4.38, dt, H-4''' | 5.31, s, H-1''' | 4.37, td, H-4''' |
|  | 3.89, s, $OCH_3$-8 |  | 3.88, s, $OCH_3$-8 |
|  | 3.50, s, $OCH_3$-2''' |  | 3.5, s, $OCH_3$-2''' |

Example 3

Compounds A and B are cytostatic and cytotoxic for human tumour cell lines (a) Compounds A and B were identified from a bark sample of Aglaia leptantha through their ability to inhibit production of Tumour Necrosis Factor-α (TNF-α) by THP-1 human promonocytic leukemia cells (Tsuchiya, et al, *Int. J. Cancer*, 1980, 26(2):171–6) activated with lipopolysaccharide (LPS). Table 4 summarises the results comparing the activity of Compounds A and B for inhibition of TNF-α production to their effects on general cell metabolism measured using WST-1 reduction, DNA synthesis and protein synthesis assays for THP-1 cells. Compounds A and B potently inhibited TNF-α production at broadly similar concentrations that were active in the WST-1 reduction, DNA and protein synthesis assays. For comparison, the effects of Compounds A and B on A549 lung epithelial carcinoma cells (Leiber et al, *Int. J. Cancer*, 1976, 17(1)-62–70) were also measured and the data is also included in Table 4. Compounds A and B are significantly less potent for inhibition of interleukin-1 (IL-1)-induced Intercellular Adhesion Molecule-1 (ICAM-1) expression by A549 cells even though in these cells the protein and DNA synthesis inhibition occur at broadly similar concentrations as for THP-1 cells.

TABLE 4

Comparison of the effects of Compounds A and B in THP-1 and A549 Cells*

| | $IC_{50}$ (µM) | | | | | | |
|---|---|---|---|---|---|---|---|
| | THP-1 cells | | | | A549 cells | | |
| Compound | TNF-a Production | WST-1 Reduction | Protein SynThesis | DNA Synthesis | ICAM-1 Production | Protein Synthesis | DNA Synthesis |
| Compound A | 0.06 | 0.03 | 0.06 | 0.015 | 2 | 0.02 | 0.007 |
| Compound B | 0.015 | 0.04 | 0.003 | 0.003 | 5 | 0.01 | 0.004 |

*Purified Compound A or Compound B solubilized in DMSO were tested over a range of concentrations in parallel for inhibitory activity in the various assays in both THP-1 and A549 cells. The concentration that resulted in a 50% inhibition of the relevant response ($IC_{50}$) is shown. Production of TNFα by THP-1 cells was measured as that released into the culture supernatant over 18 hours by sandwich enzyme-linked immunosorbent assay (ELISA) using the following mouse anti-TNFα monoclonal antibodies (capture antibody, MAB610; detection antibody, biotinylated MAB210; both from R&D Systems, Minneapolis MN, USA). Surface expression of ICAM-1 by A549 cells was assayed after 24 hours of culture by direct antibody binding using a europium-labelled mouse anti-ICAM-1 monoclonal antibody (R&D Systems Cat No. BBA3) and measured by time-resolved fluorescence using Delfia assay (EG&G Wallac, Turku, Finland). Reduction of WST-1 (Roche, Cat. No. 1644807) by THP-1 cells was measured after 18 hours of culture according to the manufacturer's instructions. Protein synthesis was measured as the uptake of [$^{14}$C]-leucine (0.5 µCi/mL) after 48 hours for THP-1 cells and 72 hours for A549 cells cultured in growth medium (RPMI-1640, 10% FBS) containing 10% the usual L-leucine concentration (5 mg/mL). DNA synthesis was measured as the uptake off [$^{14}$C]-thymidine (0.5 µCi/mL) after 48 hours for THP-1 cells and 72 hours for A549 cells in normal growth medium.

(b) Compound A was assessed for cytotoxic and cytostatic activity against a panel of cell lines derived from a variety of human tumour types in addition to THP-1 and A549 cells (Table 5). These included K562 leukemic cells (Lozzio and Lozzio, 1975, *Blood* 45:321–34), PC3 prostate tumour cells (Kaighn et al., 1979, *Invest. Urol.* 17:16–23) and SF268 glioblastoma cells (Westphal et al, 1985, Biochem. Biophys. Res. Commun., 132:284–9). Compound A exhibited potent cytostatic activity in nearly all cell lines tested with $GI_{50}$ values ranging between 1–7 nM. Compound A also exhibited potent cytotoxic effects against the various tumour cell lines. Interestingly, the THP-1 and PC3 cells proved the most rapidly killed with little difference in $LC_{50}$ values obtained after 3 or 6 days of culture. However, the cytotoxic potency of Compound A increased dramatically after 6 days of culture for the K562, A549 and SF268 cells. It should be noted that the concentration of Compound A required to inhibit cell proliferation were significantly lower than those required to elicit a cytotoxic response. Hence, the cytostatic effect of Compound A is biochemically distinguishable from its ability to induce cell death. Table 6 shows that Compound B exhibited cytotoxic effects against the various tumour cell lines with comparable potency to that observed with Compound A.

TABLE 5

Compound A has potent cytostatic and cytotoxic activity in various human tumour cell lines in vitro*

| | | Compound A | | |
|---|---|---|---|---|
| Tumour Source | Tumour Cell Line | $GI_{50}$ (nM) (3 day cultures) | $LC_{50}$ (nM) (3 day cultures) | $LC_{50}$ (nM) (6 day cultures) |
| Leukemia | THP-1 | — | 36 | 24 |
| | K562 | 1 | >1000 | 10 |
| Lung | A549 | 7 | 914 | 21 |
| Prostate | PC3 | 5 | 18 | 12 |
| Brain | SF268 | 3 | 461 | 29 |

*Purified Compound A was tested over a range of concentrations up to a maximum of $1 \times 10^{-6}$ M (1000 nM) for cytostatic and cytotoxic activity against a panel of cell lines derived from various human tumour types as indicated. The $GI_{50}$ value represents the concentration of compound that inhibited the cell number increase (relative to untreated cells) by 50% after 3 days of culture. Relative cell number was determined by measuring cellular DNA using a fluorescent DNA-binding dye (YOYO-1) after lysing the cells with digitonin (Becker et al., Anal Biochem, 1994, 221(1) :78–84). The $LC_{50}$ value represents the concentration of compound that killed 50% of the cells. Cell death was measured as the proportion of dead cells exhibiting sub-diploid DNA content determined by flow cytometry after staining with propidium iodide (Nicoletti et al., J. Immunol. Methods, 1991, 139:271–79).

TABLE 6

Compounds A and B exhibit similar cytotoxic activity*

| | | $LC_{50}$ (nM) (6 day cultures) | |
|---|---|---|---|
| Tumour Source | Tumour Cell Line | Compound A | Compound B |
| Leukemia | THP-1 | 11 | 15 |
| | K562 | 12 | 15 |
| Lung | A549 | 15 | 12 |
| Prostate | PC3 | 12 | 12 |
| Brain | SF268 | 12 | 22 |

*The cytotoxic activity of Compounds A and B were compared for the various tumour cell lines as described in Table 5.

(c) Testing of Compound A against a much larger cell line panel in the NCI in vitro anticancer screen (Table 7) confirmed the results described above. Using a different assay methodology based on measurement of total cellular protein the results confirm that Compound A had broad and potent cytostatic effects with all of the cell lines exhibiting maximal inhibition of cell growth even at the lowest dose tested (10 nM). Consistent with the data in Table 5 the cytotoxic effects measured after 2 days of culture were more varied with $LC_{50}$ values ranging from 10 nM for COLO-205 colon tumour cells to ~90 µM for 786-0 renal tumour cells. These data indicate that Compound A had potent in vitro activity against a wide range of tumour cell lines representing a variety of different major types of cancer including leukemia, lung, colon, brain, melanoma, ovarian renal, prostate and breast tumours.

TABLE 7

Activity of Compound A measured in the NCI in vitro anticancer drug discovery screen*

| Tumour Source | Tumour Cell Line | $GI_{50}$ (nM) | $LC_{50}$ (nM) |
|---|---|---|---|
| Lung | EKVX | <10 | 23 |
| Lung | NCI-H226 | <10 | 193 |
| Lung | NCI-H460 | <10 | 38,019 |
| Lung | NCI-11522 | <10 | 2,399 |
| Colon | COLO-205 | <10 | 10 |
| Colon | HT29 | <10 | 1,000 |
| Brain | SF-268 | <10 | 1,000 |
| Brain | SF-295 | <10 | 1,230 |
| Brain | SF-539 | <10 | 1,096 |
| Brain | SNB-75 | <10 | 54 |
| Melanoma | LOX IMV1 | <10 | 1,000 |
| Melanoma | MALME-3M | <10 | 23,988 |
| Melanoma | M14 | <10 | 51 |
| Melanoma | SK-MEL-2 | <10 | 19,055 |
| Melanoma | SK-MEL-28 | <10 | 2,661 |
| Melanoma | 8K-MEL-5 | <10 | 67 |
| Melanoma | UACC-62 | <10 | 30 |
| Ovarian | IGROVI | <10 | 2,600 |
| Ovarian | OVCAR-4 | <10 | 11 |
| Ovarian | OVCAR-5 | <10 | 1,000 |
| Ovarian | OVCAR-8 | <10 | 21,878 |
| Ovarian | SK-OV-3 | <10 | 82,224 |
| Renal | 786-0 | <10 | 91,201 |
| Renal | A498 | <10 | 18,621 |
| Renal | ACHN | <10 | 31,623 |
| Renal | RXF 393 | <10 | 1,641 |
| Breast | MCF7 | <10 | 1,000 |
| Breast | MDA-MB-231/ATCC | <10 | 25,410 |
| Breast | MDA-MB-435 | <10 | 45 |
| Breast | MDA-N | <10 | 543 |
| Breast | BT-549 | <10 | 32,734 |

*Compound A was tested for activity in the National Cancer Institute in vitro anticancer drug discovery screen. For this Compound A was tested at five 10-fold dilutions ranging from $10^{-4}$M to $10^{-8}$M against a panel of different human tumour cell lines representing major types of cancer as described by Boyd and Paull, Drug Development Research, 1995, 34:91–109. Briefly, this involved a 48 hr incubation of the cells with Compound A prior to measuring the relative cell number by staining with sulforhodamine B. $GI_{50}$ values represent the concentration of Compound A that inhibited net growth of the cells by 50% compared to untreated controls. $LC_{50}$ values represent the concentration of Compound A that resulted in a net 50% loss (killing) of the cells relative to the start of the experiment. The data represent the average values from two such experiments conducted.

Example 4

Cytotoxic activity of Compound A is not shared by other known related compounds lacking dioxanyloxy substitution. Compound A' displays cytotoxic activity.

(a) Table 8 compares the cytostatic and cytotoxic effects of Compound A to three previously identified 1H-cyclopenta[b]benzofuran lignans that lack the dioxanyloxy group at the C6-position. The reference compounds are: Rocaglaol (Reference Compound 1) (Ohse et al., *J Nat Prod*, 1996, 59(7):650–52); 4'-Demethoxy-3',4'-methylenedioxyrocaglaol (Reference Compound 2) and Methyl 4'-demethoxy-3',4'-methylenedioxyrocaglate (Reference Compound 3) (Lee et al., Chem Biol Interact, 1998, 115(3):215–28). All four compounds exhibited detectable cytostatic activity in A549 cells with Compound A being the most potent followed in decreasing order by Reference Compounds 3, 2 and 1 respectively. Importantly, of the compounds tested, other than Compound A none of the Reference Compounds exhibited any appreciable cytotoxicity in either THP-1 or A549 cells at doses up to 5000 nM over the 3 day assay. Without intending to limit the invention by theory, it is suggested that the novel dioxanyloxy substitution at the C6-position is important for the cytotoxic activity exhibited by Compound A and distinguishes it from any other previously identified 1H-cyclopenta[b]benzofuran lignans.

TABLE 8

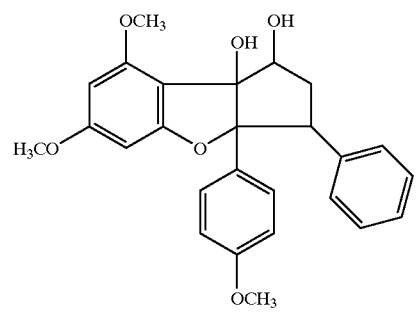

Reference Compound 1

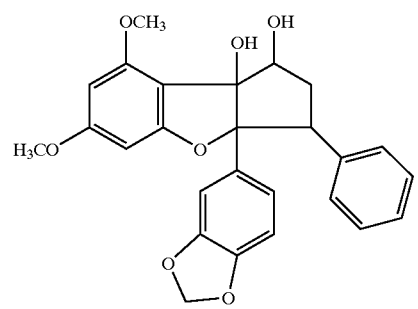

Reference Compound 2

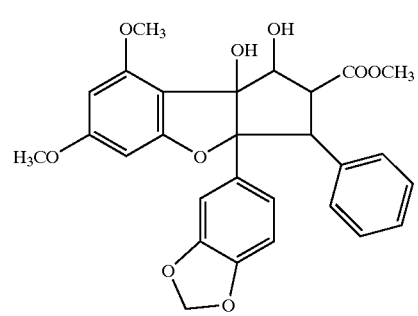

Reference Compound 3

TABLE 8-continued

Related 1H-cyclopenta[b]benzofuran lignans lacking the novel dioxanyloxy side chain do not exhibit cytotoxic activity*

| Compound | A549 cells | | THP-1 cells |
|---|---|---|---|
| | $GI_{50}$ (nM) | $LC_{50}$ (nM) | $LC_{50}$ (nM) |
| Compound A | 13 | 514 | 15 |
| Reference Compound 1 | 3980 | >5000 | >5000 |
| Reference Compound 2 | 389 | >5000 | >5000 |
| Reference Compound 3 | 56 | >5000 | >5000 |

*A549 and THP-1 cells were treated with increasing concentrations of the various compounds up to a maximum of $5 \times 10^{-6}$ M (5000 nM) and the effects on cell proliferation and cell viability were determined after 3 days of culture. $GI_{50}$ values were determined by measuring relative changes in cell number using YOYO-1 as described for Table 5. $LC_{50}$ values were determined by measuring cell death as a function of loss of memebrane integrity using YOYO-1 uptake (Becker et al., Anal Biochem, 1994, 221 (1): 78–84). The structures of the reference compounds are also shown.

(b) Table 9 shows that acetylation of the dioxanyl side chain of Compounds A and B did not reduce their biological activity since Compounds A' and B' inhibited WST-1 reduction of THP-1 leukemic with at least similar potencies to the unmodified compounds. The lower $IC_{50}$ values for all the compounds depicted in this WST-1 reduction experiment compared to the values shown in Table 4 reflects the enhanced sensitivity of the cells when treated for 3 days compared to the 18 hr treatment used in the latter assay.

TABLE 9

Acetylation of the dioxanyl side chain of Compounds A and B does not inhibit their biological activity*

| Compound | $IC_{50}$(nM) |
|---|---|
| Compound A | 2.0 |
| Compound A' | 0.3 |
| Compound B | 1.5 |
| Compound B' | 0.7 |

*Purified compounds solubilized in DMSO were tested over a range of concenfrations for their effects on the reduction of WST-1 by THP-1 leukemic cells as described for Table 4 except that the cells were cultured in the presence of the various compounds for 3 days prior to measuring WST-1 reduction.

Example 5

Compound A has acute protein synthesis inhibitory activity

Compound A was also examined to determine whether it could rapidly inhibit general protein biosynthesis. Using [$^{14}$C] leucine incorporation into insoluble cellular material as an assay for general protein biosynthesis, Table 9 shows that Compound A had an inhibitory effect evident within 3 hrs after addition to THP-1 cells with an $IC_{50}$ of ~30 nM. DNA synthesis measured over the same time was also inhibited, but less potently ($IC_{50}$~70 nM) and may be secondary to protein synthesis inhibition. Cyloheximide, a known protein synthesis inhibitor (Obrig et al, 1971, J. Biol. Chem. 246(1): 174–181), also inhibited both protein and DNA synthesis with Compound A being significantly more potent than cycloheximide in its effects. Table 10 shows that Compound A also inhibited general protein synthesis in A549 cells with an $IC_{50}$ of ~30 nM which is similar to that observed in the THP-1 cells

TABLE 10

Compound A inhibits general protein biosynthesis*

| | IC$_{50}$ (nM) | | |
|---|---|---|---|
| | THP-1 cells | | A549 cells |
| Compound | Protein synthesis | DNA Synthesis | Protein synthesis |
| Compound A | 27 | 72 | 32 |
| Cycloheximide | 263 | 303 | 238 |

*THP-1 cells and A549 cells were pretreated with the indicated concentrations of Compound A for 1 hour prior to the addition of (1 μCi/mL) [$^{14}$C] leucine (protein synthesis) or [$^{14}$C] thymidine (DNA synthesis) for a further 2 hours. The IC$_{50}$ values represent the concentration of Compound A required to inhibit incorporation of isotope by 50% relative to untreated control cell cultures.

Example 6

Compound A induces differentiation of human leukemic cell lines.

In the experiments with the THP-1 monocytic leukemia cells, which normally grow unattached in suspension, we noticed that prolonged exposure of the cells to 10 nM Compound A resulted in accumulation of cells that adhered to the plastic and exhibited numerous pseudopodia (FIG. 1). This is a morphology highly characteristic of mature macrophages and similar morphological effects were observed when the cells were treated with other known inducers of macrophage differentiation including interferon-γ (IFNγ) or phorbol 12-myristate 13-acetate (PMA). To investigate this further the effects of Compound A on HL60 human promyelocytic leukemic cells (Collins, et al, Nature, 1977, 270:347–9) were examined (Table 11). This widely used line is well characterised as a model of human myelomonocytic differentiation (Collins, Blood, 1987, 70(5):1233–44). In this experiment monocytic differentiation was quantitated by measuring CD14 surface antigen expression by flow cytometric analysis CD14, all LPS-binding protein, is expressed on the surface of cells of the myelomonocytic lineage and is normally expressed at very low levels in undifferentiated HL60 cells (Ferrero et al., Blood, 1983, 61(1):171–9). Consistent with the THP-1 data above, Table 10 shows that Compound A at doses greater than 10 nM significantly enhanced CD14 expression in the viable HL60 cells remaining after 4 days of culture. Taken together these data strongly indicate that Compound A has the ability to induce differentiation of human leukemic cell lines.

TABLE 11

Compound A promotes monocytic differentiation of HL60 leukemic cells*

| Compound A concentration (nM) | % cells expressing CD14 |
|---|---|
| 0 | 1.3% |
| 5 | 3.3% |
| 10 | 5.7% |
| 25 | 46.0% |
| 50 | 43.0% |

TABLE 11-continued

Compound A promotes monocytic differentiation of HL60 leukemic cells*

| Compound A concentration (nM) | % cells expressing CD14 |
|---|---|

*HL60 cells were cultured for 4 days with the indicated concentration of Compound A then collected and fixed in 70% ethanol. Cells were then stained with mouse monoclonal anti CD14 antibody (OKM1) and this was measured using FITC-conjugated goat anti-mouse IgG1 as a secondary antibody. Stained cells were visualised by flow cytometry and analysis was restricted to cells judged viable at the time of fixing based on their forward and side light-scatter characteristics. Non specific staining of cells was controlled for by incubating with secondary antibody only.

Example 7

Cytostatic activity of Compound A is associated with a general inhibition of cell cycle progression in A549 cells DNA content analysis of THP-1 cells treated with varying concentrations of Compound A (FIG. 2) demonstrated that at 10 nM it was only weakly cytotoxic (increased accumulation of dead cells from 7% to 17%) and under these conditions caused cells to accumulate in the G0/G1 phases of the cell cycle. This indicates that Compound A also has cytostatic activity in THP-1 cells. For comparison, FIG. 2 shows that the microtubule destabilising drug paclitaxel (Sorger et al., Curr Opin Cell Biol, 1997, 9(6):807–14) which also induced THP-1 cell death, caused cells to accumulate in the G2/M phases of the cell cycle.

The cytostatic effect of Compound A on the proliferation of A549 cells was confirmed by directly counting the number of cells at intervals over a nine day period (FIG. 3). When compared to untreated cells 10 nM Compound A prevented the increase in cell number by more than 95% with fewer than 10% dead cells observed at this time (measured by trypan blue exclusion). Thus, under these conditions the decreased cell number can not simply be accounted for by increased cell death. A significant inhibition of cell number was seen within 2 days indicating that Compound A acts in a rapid manner. At the higher concentrations of 50 nM and 250 nM Compound A had cytotoxic effects and increased cell death to 86% and 100% respectively after 9 days and accounts for the decline in cell number to levels below the original staring number at this time. At the non-cytotoxic concentration of 10 nM, Compound A has a rapid and potent cytostatic effect on A549 cells.

To help identify a potential mechanism for the effects of Compound A, DNA content analysis was performed to determine where in the cell cycle it exerted its effect (FIG. 4). Cell cycle analysis of A549 cells treated with Compound A for 6 days showed that at 10 nM, where no obvious cytotoxicity was evident, there was a minor decline in the proportion of cells in the G0/G1 phases of the cell cycle with a concomitant increase in cells in the G2/M phases. Taken together with the growth curve data in FIG. 3 above, these data indicate that 10 nM Compound A results in a general lengthening of all phases of the cell cycle with perhaps a slightly more pronounced elongation of the G2/M phases. This contrasts to the effects of paclitaxel a drug known to act selectively at the G2/M phases of the cell cycle (FIG. 4). As the concentration of Compound A was increased and its cytotoxic effects became evident the proportion of cells in the S and G2/M phases decreased with a corresponding rise in cells in G0/G1 phases. Although there was little difference in the number of dead cells between 50 nM and 250 nM the higher dose resulted in a greater accumulation of cells in the G0/G1 phases of the cell cycle. Thus, compared to THP-1 cells (see FIG. 2) higher concentrations of Compound A are required to inhibit progression through the G0/G1 phases of the cell cycle in A549 cells.

K562 leukemic cells treated with 10–15 nM Compounds A or B exhibited a characteristic accumulation of cells in G2/M phases of the cell cycle (FIG. 5). This occurred over a narrow range of concentrations since Compounds A or B at less than 5–8 nM or more than 25 nM did not cause a G2/M phase accumulation. These data indicate that different cell lines can vary in their sensitivity and responses to Compounds A and B for cell cycle phase-specific effects.

Example 8

The cytostatic effect of Compound A is reversible in A549 cells

The reversibility of the effects of Compound A was determined. For this, A549 cells remained untreated or were cultured in the presence of various concentrations of Compound A or with paclitaxel for 5 days prior to removal of the compounds and the cells cultured for a further 4 days prior to determining cell number (FIG. 6). 10 nM of Compound A significantly suppressed the increased cell number for up to 9 days without significant cytotoxicity. However, for these cultures when Compound A was removed after 5 days there was over a five-fold increase in cell number over the subsequent 4 days of culture, representing 2–3 population doublings. The effects of treatments which were deleterious to the cells, such as higher concentrations of Compound A or the presence of paclitaxel, were not reversed upon their removal.

Example 9

Compound A inhibits cell cycle-dependent cytotoxicity elicited by various anti-cancer agents To further examine the cell cycle effects of Compound A a cytostatic concentration of this compound was combined together with other anti-cancer agents known to act at specific points in the cell cycle to see if Compound A could perturb their cell cycle-dependent effects. Cell viability was assayed after 3 days by measuring exclusion of the fluorescent DNA-binding dye YOYO-1. (Becker et al., *Anal Biochem*, 1994, 221(1):78–84). A549 cells were treated with 10 nM non-cytotoxic dose of Compound A in the presence of increasing concentrations of camptothecin and paclitaxel. Camptothecin is an inhibitor of DNA topoisomerase 1, an enzyme required for DNA replication, and results in pertubation of the S phase of the cell cycle with subsequent cell death due to activation of an S phase checkpoint (Darzynkiewicz et al., *Ann N Y Acad Sci*, 1996, 803:93–100). Paclitaxel, as already mentioned, inhibits microtubule function required for formation of the mitotic spindle thereby resulting in activation of an M phase checkpoint and subsequent cell death (Sorger et al., Curr Opin Cell Biol, 1997 9(6):807–14). FIG. 7 shows that 10 nM Compound A significantly reduced the cytotoxic effects of both camptothecin and paclitaxel even when these drugs were added at up to a 2000-fold excess. Compound A may, in a dominant manner, prevent the cell cycle-dependent cytotoxic effects of camptothecin and paclitaxel.

This was examined in more detail using DNA content analysis to specifically measure cell cycle progression and cell death. In this experiment in addition to camptothecin and paclitaxel cells were also treated with vinblastin (another microtubule inhibitor) (Sorger et al., 1997, supra) and staurosporine (a kinase inhibitor) (Gescher, *Crit Rev Oncol Hematol.*, 2000, 34(2):127–35). As previously found, A549 cells treated with 10 nM Compound A showed a minor decrease in cells in G0/G1 with a slight increase in G2/M phase cells with no detectable increase in cell death over the three days of culture (FIG. 8). Consistent with its known mechanism of action camptothecin resulted in accumulation of cells in S phase of the cell cycle and also increased the level of dead cells detected as those with a sub-diploid DNA content. Also as expected, both vinblastin and paclitaxel resulted in the majority of cells arresting in the G2/M phases of the cell cycle and increased appearance of sub-diploid dead cells. However, for all of these agents the presence of 10 nM Compound A prevented their characteristic cell cycle arrest and significantly inhibited their cytotoxic effects, dramatically reducing the appearance of sub-diploid dead cells. In contrast, Compound A had little effect on the cytotoxic effects of staurosporine, an agent which appears capable of killing cells at all active phases of the cell cycle.

Example 10

Cytostatic effects of Compound A do not correlate with a biomarker for replicative senescence.

The dramatically decreased growth rate of A549 cells cultured in the presence of 10 nM Compound A (see FIG. 3) led to the consideration of the possibility that this compound was inducing replicative senescence of these immortal tumour cells. Consistent with this possibility under these conditions A549 cells with a morphology highly suggestive of a senescent phenotype were often observed, being highly flattened with an enlarged surface area compared to their usual appearance (compare for example FIG. 9 subpanels a and b). This was evaluated further by measuring senescence-associated β-galactosidase (SA-β-gal) activity, a biomarker previously described to correlate well with senescence of human cells (Dimri et al., *Proc Natl Acad Sci USA* 1995 92(20):9363–7). Recently, it has been found that some anti-cancer agents that act by diverse mechanisms, including doxorubicin, cisplatin, cytarabine, etoposide and paclitaxel, can all induce SA-β-gal activity in a variety of tumour cell lines (Chang et al., *Cancer Res* 1999, 59(15):3761–7). Therefore, in addition to Compound A A549 cells were also treated with doxorubicin as an experimental control. This drug acts by stabilising DNA/topoisomerase II complexes thereby causing DNA damage which results in subsequent S phase cell cycle arrest and/or cell death (Froelich-Ammon and Osheroff, 1995, *J. Biol. Chem.* 270(37):21429–21432). FIG. 9 shows that consistent with the earlier report A549 cells treated with 250 nM doxorubicin displayed the flattened enlarged phenotype of senescent cells and exhibited SA-β-gal activity. In contrast, Compound A at various doses from 10–50 nM failed to induce SA-β-gal activity even though the cells exhibited the flattened enlarged morphology. Thus, in contrast to a variety of other anti-cancer drugs the cytostatic effects of Compound A do not correlate with this particular marker of cell senescence.

Example 11

Compound A inhibits cell proliferation but not increased cell size

It is well known that cell proliferation and cell growth reflected as increased mass of individual cells are biochemically separable processes (Pardee, *Science,* 1989, 246:603–8). Although at certain concentrations Compound A can inhibit cell proliferation without overt cytotoxicity it was also evaluated whether Compound A also affected cell growth. For these experiments A549 cells were treated with various non-cytotoxic doses of Compound A up to 10 nM and the relative cell size determined after 6 days of culture by measuring forward light scatter using a flow cytometer. The data depicted in Table, 11 show that in the presence of Compound A A549 cells exhibited an increase in the mean forward scatter by over 20%. This occurred only at concentrations which are cytostatic for this cell type.

TABLE 12

Compound A increases cell size*

| Compound A concentration (nM) | % increase in mean cell volume |
|---|---|
| 0 | — |
| 2.5 | 10.4% |
| 5.0 | 10.7% |
| 10.0 | 22.4% |

*A549 cells cultured for six days with the various non-cytotoxic concentrations of Compound A as indicated were examined by flow cytometry for their forward light scatter characteristics which directly relates to cell size. The % increase in mean cell volume represents the relative change in the mean forward scatter value for the treated versus untreated cell populations.

Example 12

Compound A inhibits growth of human tumour cell lines in a mouse xenograft tumour model.

Figure 10A:
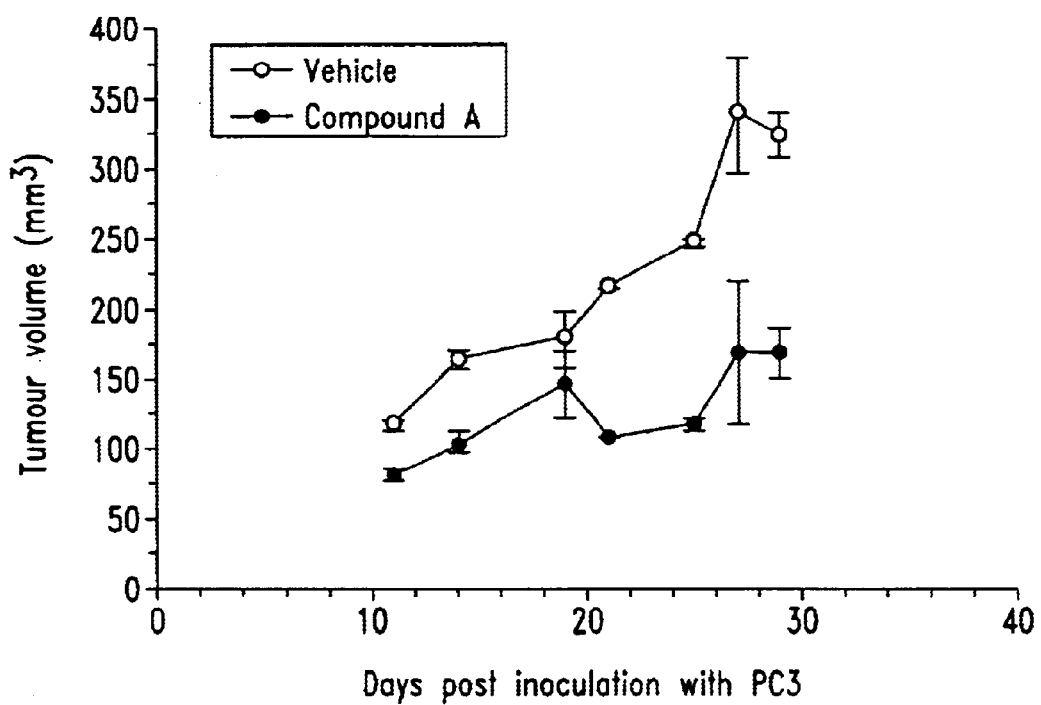
Figure 10B:
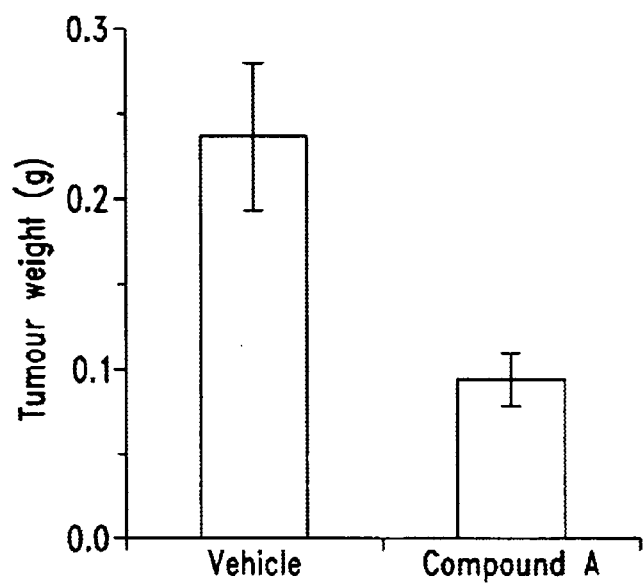

The ability of Compound A to inhibit growth of human tumour cells in vivo was assessed using male athymic mice injected subcutaneously in the dorsal flank region with $2 \times 10^6$ PC3 human prostate tumour cells. Compound A administration (3 mg/kg) by intraperitoneal injection commenced after eight days once the PC3 tumour was palpable and continued three times a week until 29 days after the initial inoculation of the tumour cells. At this time all mice were killed and tumours excised and weighed. FIG. 10A shows that compared to the control animals treated with vehicle alone the mice treated with Compound A displayed a greatly reduced increase in mean tumour volume over the course of the experiment. This was confirmed at the end of the experiment when tumours were excised and weighed it was found that Compound A treatment reduced the mean tumour weight by ~60% (FIG. 10B). Body weight was unaffected with both control and treated groups exhibiting a similar ~12% decrease in mean body weight over the duration of the experiment. Thus, Compound A exhibits in vivo antitumour activity.

We claim:

1. A compound of Formula (I):

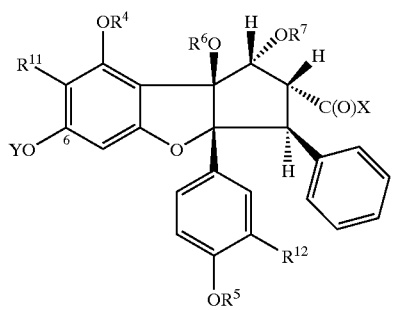

(I)

wherein:
each $R^4$–$R^{10}$ is independently selected from the group consisting of hydrogen, optionally substituted alkyl, optionally substituted acyl, optionally substituted aryl, optionally substituted arylalkyl, optionally substituted cycloalkylalkyl, optionally substituted arylacyl, optionally substituted cycloalkylacyl and a C-1 linked saccharide;

X is $OR^8$ or $NR^9R^{10}$;
$R^{11}$ and $R^{12}$ are each independently hydrogen or, $OR^4$ and $R^{11}$, and/or $OR^5$ and $R^{12}$ together form a methylenedioxy group; and
Y is selected from the group consisting of optionally substituted phenyl, optionally substituted benzyl, optionally substituted benzoyl, optionally substituted $C_3$–$C_8$ cycloalkyl, optionally substituted $CH_2$-($C_3$–$C_8$ cycloalkyl), optionally substituted 5–6 membered heterocyclyl and optionally substituted $CH_2$-(5–6 membered heterocyclyl);
or a salt, isomer or prodrug thereof.

2. The compound according to claim 1 wherein $R^4$ and Y are independently selected from the group consisting of optionally substituted $C_3$–$C_8$ cycloalkyl, optionally substituted benzoyl, optionally substituted benzyl, optionally substituted $CH_2$-($C_3$–$C_8$ cycloalkyl) and C-1 linked saccharide.

3. The compound according to claim 1 wherein the optionally substituted $C_3$–$C_8$ cycloalkyl group is optionally substituted $C_5$–$C_6$-cycloalkyl and the optionally substituted $CH_2$-($C_3$–$C_8$ cycloalkyl) group is optionally substituted $CH_2$-($C_5$–$C_6$ cycloalkyl).

4. The compound according to claim 1 wherein Y is an optionally substituted 5–6 membered heterocyclyl group or an optionally substituted $C_5$–$C_6$ cycloalkyl group.

5. The compound according to claim 4 having Formula (i)

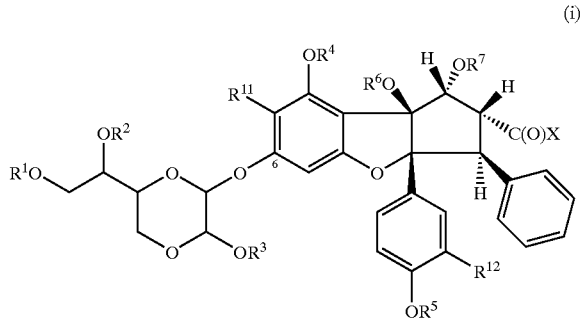

(i)

or isomer thereof,
wherein:
each $R^1$–$R^{10}$ is independently selected from the group consisting of hydrogen, optionally substituted alkyl, optionally substituted acyl, optionally substituted aryl, optionally substituted arylalkyl, optionally substituted cycloalkylalkyl, optionally substituted arylacyl, optionally substituted cycloalkylacyl and a C-1 linked saccharide;
X is $OR^8$ or $NR^9R^{10}$, and
$R^{11}$ and $R^{12}$ are each independently hydrogen or $OR^4$ and $R^{11}$, and/or $OR^5$ and $R^{12}$ together form a methylenedioxy group.

6. The compound according to claim 1 or 5 wherein $R^8$ is selected from the group consisting of hydrogen, $C_{1-6}$ alkyl, phenyl, benzyl and C-1 linked saccharide.

7. The compound according to claim 1 or 5 wherein $R^9$ and $R^{10}$ are independently selected from the group consisting of hydrogen, $C_{1-6}$ alkyl, phenyl and benzyl.

8. The compound according to claim 1 or 5 wherein $R^{11}$ and $R^{12}$ are both hydrogen.

9. The compound according to claim 5 wherein each of $R^1R^7$ are independently selected from the group consisting of hydrogen, methyl, ethyl, n-propyl, i-propyl, n-butyl, sec-butyl, t-butyl, cyclopropylmethyl, cyclopropylethyl, cyclobutylmethyl, cyclobutylethyl, cyclopentylmethyl, cyclopentylethyl, cyclohexylmethyl, cyclohexylethyl, phenyl, benzyl, acetyl and C-1 linked saccharide.

10. The compound according to claim 5 wherein $R^1$ and $R^2$ are both hydrogen.

11. The compound according to claim 5 wherein $R^3$ is methyl.

12. The compound according to claim 5 wherein at least one of $R^3$–$R^5$ is methyl, ethyl or propyl.

13. The compound according to claim 12 wherein at least one of $R^3$–$R^5$ is methyl.

14. The compound according to claim 12 wherein at least two of $R^3$–$R^5$ are methyl, ethyl or propyl.

15. The compound according to claim 14 wherein at least two of $R^3$–$R^5$ are methyl.

16. The compound according to claim 14 wherein all of $R^3$–$R^5$ are methyl, ethyl or propyl.

17. The compound according to claim 16 wherein all of $R^3$–$R^5$ are methyl.

18. The compound according to claim 1 or 5 wherein $R^6$ and $R^7$ are both hydrogen.

19. The compound according to claim 1 or 5 wherein X is $OR^8$ and where $R^8$ is selected from the group consisting of hydrogen, methyl, ethyl and propyl.

20. The compound according to claim 19 wherein $R^8$ is methyl.

21. The compound according to claim 1 or 5 wherein X is $NR^9R^{10}$ where $R^9$ and $R^{10}$ are both hydrogen or methyl; or $R^9$ and $R^{10}$ are different but at least one of $R^9$ or $R^{10}$ is hydrogen and the other is $C_{1-6}$ alkyl.

22. The compound according to claim 21 wherein $C_{1-6}$ alkyl is methyl, ethyl or propyl.

23. The compound according to claim 5 having Formula (ii):

(ii)

or isomer thereof.

24. The isomer of the compound of claim 23 having the following NMR spectral characteristics:

$^1$H NMR (CDCl$_3$, ppm)

3.49, s, 3H; 3.56, dd, 11.7, 2 Hz, 1H; 3.61, m, 1H, 3.61, 2H; 3.65, s, 3H; 3.71, s, 3H; 3.87, s, 3H; 3.89, dd, 14.2, 6.7 Hz, 1H; 4.13, t, 11.2 Hz, 1H 4.23, brt, 11.3 Hz, 1H; 4.28, d, 14.2 Hz, 1H; 4.59, s, 1H; 5.03, d, 6.7 Hz, 1 Hz; 5.28, s, 1H; 6.28, d, 2 Hz, 1H; 6.43, d, 2 Hz, 1H; 6.68, brd, 9 Hz, 2H; 6.84, m, 2H; 7.06, m, 2H, 7.06, m, 1H; 7.10, brd, 9 Hz, 2H;

$^{13}$C NMR (CDCl$_3$), (ppm)

50.03, 52.06, 55.03, 55.05, 55.1, 55.9, 59, 63.3, 68.3, 70.6, 79.6, 92.8, 93.4, 93.9, 94, 95.2, 101.9, 109.6, 112.7, 126.2, 126.6, 127.8, 127.8, 128.9, 136.7, 157.1, 158.8, 160, 160.6, 170.6.

25. The isomer of the compound of claim 23 having the following NMR spectral characteristics:

$^1$H NMR (CDCl$_3$, ppm)

3.5, s, 3H; 3.61, dd, 10.4, 4.4 Hz, 1H; 3.66, m, 1H; 3.66, s, 3H; 3.72, m; 3.72, s, 3H; 3.78, dd, 11.7, 2.4 Hz, 1H; 3.86, s, 3H; 3.9, dd, 14, 6.8 Hz, 1H; 4.02, t, 11.2 Hz, 1H; 4.12, ddd, 11, 6.8, 2–8 Hz, 1H; 4.28, d, 14 Hz, 1H; 4.60, S, 1H; 5.04, d, 6.8 Hz, 1 H; 5.26, S, 1H; 6.29, d, 2 Hz, 1H; 6.45, d, 2 Hz, 1H; 6.69, brd, 9 Hz, 2H; 6.86, m, 2H; 7.06, m, 2H; 7.06, m, 1H; 7.10, brd, 9 Hz, 2H;

$^{13}$C NMR (CDCl$_3$), (ppm)

50, 52, 55, 55, 55, 55.8, 59.6, 62.5, 67.6, 71.4, 79.6, 92.8, 93.4, 94.3, 95.2, 101.8, 109.4, 112.8, 126.2, 126.6, 127.5, 127.5, 128.9, 136.6, 157.1, 158.8, 159.8, 160.2, 170.7.

26. A composition comprising a compound of claim 1 together with a pharmaceutically acceptable carrier excipient or diluent.

27. The composition according to claim 26 wherein the compound is of Formula (i) as defined in claim 5 or (ii) as defined in claim 23.

28. A method for the treatment of cancer or a cancerous condition wherein the cancer or cancerous condition is selected from the group consisting of leukemia, sarcoma, breast, colon, bladder, pancreatic, endometrial, head and neck, mesothelioma, myeloma, oesophagal/oral, testicular, thyroid, cervical, bone, renal, uterine, prostate, brain, lung, ovarian, skin, liver and bowel and stomach cancers, tumours and melanomas, comprising the administration of a treatment effective amount of a compound according to claim 1 to a subject in need thereof.

29. The method according to claim 28 wherein the compound is of Formula (i) as defined in claim 5 or (ii) as defined in claim 23.

30. A method for the treatment of a disease state or condition associated with cellular hyperproliferation wherein the disease state or condition is selected from the group consisting of atherosclerosis, restinosis, rheumatoid arthritis, osteoarthritis, inflammatory arthritis, psoriasis, periodontal disease and virally induced cellular hyperproliferation, comprising the administration of a treatment effective amount of a compound of claim 1 to a subject in need thereof.

31. The method according to claim 30 wherein the compound is of Formula (i) as defined in claim 5 or (ii) as defined in claim 23.

32. A composition comprising the isomer according to claim 24 or 25 together with a pharmaceutically acceptable carrier, excipient or diluent.

33. A method for the treatment of cancer or a cancerous condition wherein the cancer or cancerous condition is selected from the group consisting of leukemia, sarcoma, breast, colon, bladder, pancreatic, endometrial, head and neck, mesothelioma, myeloma, oesophagal/oral, testicular, thyroid, cervical, bone, renal, uterine, prostate, brain, lung, ovarian, skin, liver and bowel and stomach cancers, tumours and melanomas, comprising the administration of a treatment effective amount of the isomer according to claim 24 or 25 to a subject in need thereof.

34. A method for the treatment of a disease state or condition associated with cellular hyperproliferation wherein the disease state or condition is selected from the group consisting of atherosclerosis, restinosis, rheumatoid arthritis, osteoarthritis, inflammatory arthritis, psoriasis, peridontal disease and virally induced cellular hyperproliferation, comprising the administration of a treatment effective amount of the isomer a according to claim 24 or 25 to a subject in need thereof.

* * * * *